US008709800B2

(12) United States Patent
Kubota et al.

(10) Patent No.: US 8,709,800 B2
(45) Date of Patent: *Apr. 29, 2014

(54) METHODS OF ISOLATING BIPOTENT HEPATIC PROGENITOR CELLS

(75) Inventors: Hiroshi Kubota, Chapel Hill, NC (US); Lola M. Reid, Chapel Hill, NC (US)

(73) Assignee: University of North Carolina at Chapel Hill, Chapel Hill, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 12/265,381

(22) Filed: Nov. 5, 2008

(65) Prior Publication Data

US 2009/0068735 A1  Mar. 12, 2009

Related U.S. Application Data

(63) Continuation of application No. 11/757,168, filed on Jun. 1, 2007, now abandoned, which is a continuation of application No. 09/678,953, filed on Oct. 3, 2000, now abandoned.

(60) Provisional application No. 60/157,052, filed on Oct. 1, 1999.

(51) Int. Cl.
 *C12N 5/00* (2006.01)
 *C12N 15/09* (2006.01)

(52) U.S. Cl.
 USPC .......................................... 435/325; 435/455

(58) Field of Classification Search
 USPC ................................................ 435/325, 455
 See application file for complete search history.

(56) References Cited

U.S. PATENT DOCUMENTS

| | | | |
|---|---|---|---|
| 3,819,991 | A | 6/1974 | Weigele et al. |
| 4,382,308 | A | 5/1983 | Curcio |
| 4,914,032 | A | 4/1990 | Kuri-Harcuch et al. |
| 5,475,889 | A | 12/1995 | Thrasher et al. |
| 5,486,129 | A | 1/1996 | Sandhu et al. |
| 5,510,254 | A | 4/1996 | Naughton et al. |
| 5,559,022 | A | 9/1996 | Naughton et al. |
| 5,576,207 | A | 11/1996 | Reid et al. |
| 5,679,340 | A | 10/1997 | Chappel |
| 5,700,180 | A | 12/1997 | Sandhu et al. |
| 5,743,784 | A | 4/1998 | Birang et al. |
| 5,846,882 | A | 12/1998 | Birang |
| 5,866,420 | A | 2/1999 | Talbot et al. |
| 5,901,400 | A | 5/1999 | Fulop |
| 5,943,726 | A | 8/1999 | Eitoku et al. |
| 6,004,810 | A | 12/1999 | Tateno et al. |
| 6,059,888 | A | 5/2000 | Hillman |
| 6,070,284 | A | 6/2000 | Garcia et al. |
| 6,129,911 | A | 10/2000 | Faris |
| 6,143,089 | A | 11/2000 | Stephens et al. |
| 6,269,510 | B1 | 8/2001 | Beardsley et al. |
| 6,330,728 | B2 | 12/2001 | Ueki et al. |
| 6,352,596 | B2 | 3/2002 | Beardsley et al. |
| 6,425,158 | B2 | 7/2002 | Ravkin |
| 6,493,896 | B1 | 12/2002 | Stuchlik et al. |
| 6,572,710 | B2 | 6/2003 | Middendorf et al. |
| 6,615,433 | B2 | 9/2003 | Crevasse et al. |
| 6,623,334 | B1 | 9/2003 | Birang et al. |
| 6,739,013 | B2 | 5/2004 | Glashauser et al. |
| 6,887,129 | B2 | 5/2005 | Birang |
| 7,229,504 | B2 | 6/2007 | Sugarman et al. |
| 7,456,017 | B2 | 11/2008 | Kubota et al. |
| 2001/0001886 | A1 | 5/2001 | Ueki et al. |
| 2002/0005212 | A1 | 1/2002 | Beardsley et al. |
| 2002/0139393 | A1 | 10/2002 | Crevasse et al. |
| 2002/0187133 | A1 | 12/2002 | Kubota et al. |
| 2003/0000550 | A1 | 1/2003 | Middendorf et al. |

(Continued)

FOREIGN PATENT DOCUMENTS

| | | |
|---|---|---|
| CA | 2336958 A1 | 1/2000 |
| CA | 2 248 459 A1 | 3/2000 |

(Continued)

OTHER PUBLICATIONS

"ATCC Cell Lines and Hybridomas," American Type Culture Collection, *ATTC Catalogue*, 8th Ed., 1994, pp. 146, 516, 518, 519, 534.
"ATCC Cell Lines and Hybridomas," American Type Culture Collection, *ATCC Catalogue*, 8th Ed., 1994. p. 522.
Baumann et al., "Expression of the Stem Cell Factor Receptor c-kit in Normal and Diseased Pediatric Liver: Identification of a Human Hepatic Progenitor Cell?," *Hepatology*, Jul. 1999, vol. 30, No. 1, pp. 112-117.

(Continued)

*Primary Examiner* — Marcia S Noble
*Assistant Examiner* — Magdalene Sgagias
(74) *Attorney, Agent, or Firm* — Gilberto M. Villacorta; Sunit Talapatra; Foley & Lardner LLP

(57) ABSTRACT

A method of obtaining a mixture of cells enriched in hepatic progenitors is developed which comprises methods yielding suspensions of a mixture of cell types, and selecting those cells that are classical MHC class I antigen(s) negative and ICAM-1 antigen positive. The weak or dull expression of nonclassical MHC class I antigen(s) can be used for further enrichment of hepatic progenitors. Furthermore, the progenitors can be selected to have a level of side scatter, a measure of granularity or cytoplasmic droplets, that is higher than that in non-parenchymal cells, such as hemopoietic cells, and lower than that in mature parenchymal cells, such as hepatocytes. Furthermore, the progeny of the isolated progenitors can express alpha-fetoprotein and/or albumin and/or CK19. The hepatic progenitors, so isolated, can grow clonally, that is an entire population of progeny can be derived from one cell. The clones of progenitors have a growth pattern in culture of piled-up aggregates or clusters. These methods of isolating the hepatic progenitors are applicable to any vertebrates including human. The hepatic progenitor cell population is expected to be useful for cell therapies, for bioartificial livers, for gene therapies, for vaccine development, and for myriad toxicological, pharmacological, and pharmaceutical programs and investigations.

21 Claims, 15 Drawing Sheets

(56) References Cited

U.S. PATENT DOCUMENTS

| | | |
|---|---|---|
| 2003/0131872 A1 | 7/2003 | Nishihara |
| 2003/0175255 A1 | 9/2003 | Kubota et al. |
| 2007/0231853 A1 | 10/2007 | Kubota et al. |
| 2007/0238172 A1 | 10/2007 | Kubota et al. |
| 2009/0053758 A1 | 2/2009 | Kubota et al. |
| 2009/0104626 A1 | 4/2009 | Kubota et al. |

FOREIGN PATENT DOCUMENTS

| | | |
|---|---|---|
| EP | 0 682 106 A2 | 11/1995 |
| EP | 1 097 193 B1 | 12/2006 |
| GB | 2 276 537 A | 10/1994 |
| JP | 7-501206 A | 2/1995 |
| JP | 8-112092 A | 5/1996 |
| JP | 8-508891 A | 9/1996 |
| JP | 11-507227 A | 6/1999 |
| WO | WO 95/00632 A1 | 1/1995 |
| WO | WO 96/40872 A1 | 12/1996 |
| WO | WO 00/03001 A1 | 1/2000 |
| WO | WO 00/43498 A2 | 7/2000 |
| WO | WO 02/028997 A2 | 4/2002 |
| WO | WO 02/29012 A1 | 4/2002 |

OTHER PUBLICATIONS

Beg et al., "Embryonic Lethality and Liver Degeneration in Mice Lacking the ReIA Component of NF—κB," *Nature*, Jul. 13, 1995, vol. 376, pp. 167-170.

Bisgaard et al., "Modulation of the Gene Network Connected to Interferon-γ in Liver Regeneration from Oval Cells," *American Journal of Pathology*, Oct. 1999, vol. 155, No. 4, pp. 1075-1085.

Block et al., "Population Expansion, Clonal Growth, and Specific Differentiation Patterns in Primary Cultures of Hepatocytes Induced by HGF/SF, EFG and TFGα in a Chemically Defined (HGM) Medium," *Journal of Cell Biol.*, Mar. 1996, vol. 132, pp. 1133-1149.

Conget et al., "Phenotypical and Functional Properties of Human Bone Marrow Mesenchymal Progenitor Cells," *Journal of Cellular Physiology*, 1999, vol. 181, pp. 67-73.

Cruickshank et al., "Expression and cytokine regulation of immune recognition elements by normal human biliary epithelial and established liver cell lines in vitro," *J. Hepatology.*, 1998, vol. 29, pp. 550-558.

Cruickshank et al., "Expression of CD44 on Bile Ducts in Primary Sclerosing Cholangitis and Primary Biliary Cirrhosis," *J. Clin. Pathol.*, 1999, vol. 52, pp. 730-734.

Davis et al., "A Self-renewing Multipotential Stem Cell in Embryonic Rat Cerebral Cortex," *Nature*, Nov. 17, 1994, vol. 372, pp. 263-266.

Deonarain, "Ligand-targeted receptor-mediated vectors for gene delivery," *Exp. Opin. Ther. Patents*, 1998, vol. 8, No. 1, pp. 53-69,: Ashley Publications, Ltd.

Doi et al., "Absence of Tumor Necrosis Factor Rescues ReIA-deficient Mice from Embryonic Lethality," *Proc. Natl. Acad. Sci. USA*, Mar. 1999, vol. 96, pp. 2994-2999, 6571-6573.

Douarin, "An Experimental Analysis of Liver Development," *Medical Biol.*, 1975, vol. 53, pp. 427-455.

Dzierzak et al., "Qualitative and Quantitative Aspects of Haematopoietic Cell Development in the Mammalian Embryo," *Immunol. Today*, May 1998, vol. 19, No. 5, pp. 228-236.

Eck et al., "Gene-Based Therapy," *The Pharmacological Basis of Therapeutics*, Chapter 5, 1996, pp. 77-100.

Enat et al., "Hepatocyte Proliferation in vitro: Its Dependence on the Use of Serum-free Hormonally Defined Medium and Substrata of Extracellular Matrix," *Proc. Natl. Acad. Sci. USA*, Mar. 1984, vol. 81, pp. 1411-1415.

Fishback, "A Morphologic Study of Regeneration of the Liver After Partial Removal," *Arch. Pathol.*, Feb. 12, 1929, vol. 7, pp. 955-977.

Gage, "Cell Therapy," *Nature*, Apr. 30, 1998, vol. 392, Sup., pp. 18-24.

Ganiatsas et al., "SEK1 Deficiency Reveals Mitogen-Activated Protein Kinase Cascade Crossregulation and leads to Abnormal Hepatogensis," *Proc. Natl. Acad. Sci. USA*, Jun. 1998, vol. 95, pp. 6881-6886.

Gordon et al., "Temporal Analysis of Hepatocyte Differentiation by Small Hepatocyte-Like Progenitor Cells During Liver Regeneration in Retrorsine-Exposed Rats," *American Journal of Pathology*, Sep. 2000, vol. 157, No. 3, pp. 771-786.

Gualdi et al., "Hepatic Specification of the Gut Endoderm in vitro: Cell Signaling and Transcriptional Control," *Genes & Dev.*, 1996, vol. 10, pp. 1670-1682, Cold Spring Harbor Laboratory Press.

Günes et al., "Embryonic Lethality and Liver Degeneration in Mice Lacking the Metal-responsive Transcriptional Activator MTF-1," *EMBO J.*, 1998, vol. 17, No. 10, pp. 2846-2854.

Hall et al., "Stem Cells: the Generation and Maintenance of Cellular Diversity," *Development*, 1989, vol. 106, pp. 619-633.

Haque et al., "Identification of Bipotential Progenitor Cells in Human Liver Regeneration," *Laboratory Investigation*, Nov. 1996, vol. 75, No. 5, pp. 699-705.

Haruna et al., "Identification of Bipotential Progenitor Cells in Human Liver Development," *Hepatology*, Mar. 1996, vol. 23, No. 3, pp. 476-481.

Higgins et al., "Experimental Pathology of the Liver," *Archives of Pathology*, Jan. 20, 1931, vol. 12, pp. 186-202.

Hilberg et al., "c-Jun is Essential for Normal Mouse Development and Hepatogenesis," *Nature*, Sep. 9, 1993, vol. 365, pp. 179-181.

Hirata et al., "Effects of basement membrane matrix on the culture of fetal mouse hepatocytes," *Biological Abstracts*, Gann, Japanese Jouirnal of Cancer Research, Oct. 1983, vol. 74, No. 5, pp. 687-692.

Houlihan et al., "Evidence for the Expression of Non-HLA-A, B, C Class I Genes in the Human Fetal Liver," *J. Immunology*, 1992, vol. 149, No. 2, pp. 668-675.

Houssaint, "Differentiation of the Mouse Hepatic Primordium. I. An Analysis of Tissue Interactions in Hepatocyte Differentation," *Cell Differ.*, 1980, vol. 9, pp. 269-279.

Houssaint, "Differentiation of the Mouse Hepatic Primordium. II. Extrinsic Origin of the Haemopoietic Cell Line," *Cell Differ.*, 1981, vol. 10, pp. 243-252.

International Search Report, PCT/US00/27428 (May 21, 2001).

International Search Report, PCT/US00/27429 (May 16, 2001).

Inverardi et al., "Cell Transplantation," *Transplantation Biology: Cellular and Molecular Aspects*, Raven Publishers, Philadelphia, 1996, pp. 679-687.

Isfort et al., "The Combination of Epidermal Growth Factor and Transforming Growth Factor-Beta Induces Novel Phenotypic Changes in Mouse Liver Stem Cell Lines," *Journal of Cell Science*, Dec. 1997, vol. 110, No. 24, pp. 3117-3129.

Jefferson et al., "Posttranscriptional Modulation of Gene Expression in Cultured Rat Hepatocytes," *Mol. Cell. Biol.*, Sep. 1984, vol. 4, No. 9, pp. 1929-1934.

Jones et al., "Separation of Human Epidermal Stem Cells from Transit Amplifying Cells on the Basis of Differences in Integrin Function and Expression," *Cell*, May 21, 1993, vol. 73, pp. 713-724.

Koch et al., "Normal Liver Progenitor Cells in Culture," *Stem Cells handbook*: Chapter 33, 2004, pp. 367-384, Humana Press Inc., Totowa, NJ.

Koestenbauer et al., Embryonic Stem Cells: Similarities and Differences Between Human and Murine Embryonic Stem Cells, *American Journal of Reproductive Immunology*, 2006, vol. 55, pp. 169-180.

Kohno et al., "Ultrastructural characteristics of intercellular contacts and bile canaliculi in neonatal rat hepatocytes in primary culture," *Virchows Arch B Cell Pathol Incl Mol Pathol.*, 1993, vol. 63, No. 5, pp. 317-324.

Kubota et al., "Clonogenic Hepatoblasts Common Precursors for Hepatocytic and Biliary Lineages, are Lacking Classical Major Histocompatability Complex Class I Antigen," *PNAS*, Oct. 24, 2000, vol. 97, No. 22, pp. 12132-12137.

Langer et al., "Tissue Engineering," *Science*, May 14, 1993, vol. 260, pp. 920-926.

Laurson et al., "Hepatocyte Progenitors in Man and in Rodents—Multiple Pathways, Multiple Candidates," *Int. J. Ex. Path*, 2005, vol. 8, pp. 1-18.

Lazaro et al., "Establishment, Characterization, and Long-Term Maintenance of Cultures of Human Fetal Hepatocytes," *Hepatology*, Nov. 2003, vol. 38, No. 5, pp. 1095-1106.

Li et al., "Severe Liver Degeneration in Mice Lacking the IkB Kinase 2 Gene," *Science*, Apr. 9, 1999, vol. 284, pp. 321-325.

(56) References Cited

OTHER PUBLICATIONS

Li et al., "Isolation and Characterization of Bipotent Liver Progenitor Cells from Adult Mouse," *Stem Cells*, 2006, vol. 24, pp. 322-332.
Luzzatto, "Hepatocyte Differentiation During Early Fetal Development in the Rat," *Cell Tissue Res.*, 1981, vol. 215, pp. 133-142.
Miller, "Human Gene Therapy Comes of Age," *Nature*, Jun. 11, 1992, vol. 357, pp. 455-460.
Moll et al., "The Catalog of Human Cytokeratins: Patterns of Expression in Normal Epithelia, Tumors and Cultured Cells," *Cells*, Nov. 1982, vol. 31, pp. 11-24.
Motoyama et al., "Organogensis of the Liver, Thymus and Spleen is Affected in Jumonji Mutant Mice," *Mechanics of Dev.*, 1997, vol. 66, pp. 27-37.
Nakamura et al. "In Vitro Induction of Neonatal Rat Hepatocytes by Direct Contact with Adult Rat Heapatocytes," *Experimental Cell Research*, 1987, vol. 169, No. 1, pp. 1-14.
Nishina et al., "Defective Liver Formation and Liver Cell Apoptosis in Mice Lacking the Stress Signaling Kinase SEK1/MKK4," *Development*, 1999, vol. 126, pp. 505-516.
Nishino et al., "Hepatocyte Growth Factor as a Hematopoietic Regulator," *Blood*, Jun. 1, 1985, vol. 85, No. 11, pp. 3093-3100.
Overturf et al., "Serial Transplantation Reveals the Stem-Cell-Like Regenerative Potential of Adult Mouse Hepatocytes," *Am. J. Pathol.*, Nov. 1997, vol. 151, No. 5, pp. 1273-1280.
Parent et al., "Origin and Characterization of a Human Bipotent Liver Progenitor Cell Line," *Gastroenterology*, 2004, Vol. 126, No. 4, pp. 1147-1156.
Petersen et al., "Hepatic Oval Cells Express the Hematopoietic Stem Cell Marker Thy-1 in the Rat," *Hepatology*, Feb. 1998, vol. 27, No. 2, pp. 433-445.
Rhim et al., "Replacement of Diseased Mouse Liver by Hepatic Cell Transplantation," *Science*, Feb. 25, 1994, vol. 263, pp. 1149-1152.
Saadi et al., "Immunology of Xenotransplantation," *Life Sciences*, 1998, vol. 62, No. 5, pp. 365-387.
Sargiacomo et al., "Long-term cultures of human fetal liver cells: a three-dimensional experimental model for monitoring liver tissue development," *Journal of Hepatology*, 1998, vol. 28: pp. 480-490.
Schmidt et al., "Scatter factor/hepatocyte Growth Factor is Essential for Liver Development," *Nature*, Feb. 23, 1995, vol. 373, pp. 699-702.
Seglen, "Preparation of Isolated Rat Liver Cells," *Methods in Cell Biology*, vol. XIII, Chapter 4, Academic Press, 1976, pp. 29-83.
Shiojiri et al. "Cell Lineages and Oval Cell Progenitors in Rat Liver Development," *Can. Res.*, May 15, 1991, vol. 51, pp. 2611-2620.
Shiojiri, "Development and Differentiation of Bile Ducts in the Mammalian liver," *Microscopy Research and Technique*, 1977, vol. 39, pp. 328-335.
Sigal et al., "Characterization and Enrichment of Fetal Rat Hepatoblasts by Immunoadsorption ('Panning') and Fluorescence-activated Cell Sorting," *Hepatology*, Apr. 1994, vol. 19, No. 4, pp. 999-1006.
Spangrude et al., "Purification and Characterization of Mouse Hematopoietic Stem Cells," *Science*, Jul. 1, 1988, vol. 241, No. 4861, pp. 58-62.
Stemple et al., "Isolation of a Stem Cell for Neurons and Glia from the Mammalian Neural Crest," *Cell*, Dec. 11, 1992, vol. 71, pp. 973-985.
Tanaka et al., "Embryonic Lethality, Liver Degeneration, and Impaired NF-κB Activation in IKK-β-Deficient Mice," *Immunity*, Apr. 1999, vol. 10, pp. 421-429.
Tateno, et al., "Growth Potential and Differentiation Capacity of Adult Rat Hepatocytes in vitro," *Wound Repair and Regeneration*, Jan.-Feb. 1999, vol. 7, No. 1, pp. 36-44.
Verfaillie et al., "Stem Cells: Hype and Reality," *Amer. Soc. Hematology*, 2002, pp. 369-391.
Verma et al., "Gene therapy—Promises, Problems and Prospects," *Nature*, Sep. 18, 1997, vol. 389, pp. 239-242.
Weber et al., "Primate hepatic foetal progenitor cells and their therapeutic potential," *Pathologie Biologie*, 2006, Vo. 54, pp. 58-63.
Zhang et al., "Hepatic Stem Cells: Existence and Origin," *World Journal Gastroenterol*, Feb. 15, 2003, vol. 9, No. 2, pp. 201-204.
Curran, et al., Mitogen-Independent DNA Synthesis by Fetal Rat Hepatocytes in Primary Culture, Experimental Cell Research. vol. 209, pp. 53-57 (1993).
Geissler et al., "Secreted Donor-MHC Class I Antigen Prolongs Liver Allograft Survival and Inhibits Recipient Anti-Donor Cytotoxic T Lymphocyte Responses", Department of Medical Technology, University of South Alabama.
Hirozane et al., "Analysis of the MHC Class 1 antigen of the rat salivary gland", J. Jpn. Stomatol. Soc. 37(3): 548-553, Jul. 1988.
Mitaka et al., "Multiple Cell Cycles Occur in Rat Hepatocytes Cultured in the Presence of Nicotinamide and Epidermal Growth Factor".
Satoh et al., "Proinflammatory cytokines and endotoxin stimulate ICAM-1 gene expression and secretion by normal human hepatocytes", Immunology 1994, pp. 571-576.
Tateno et al., "Heterogeneity of Growth Potential of Adult Rat Hepatocytes in Vitro".
Geissler et al., "Secreted Donor-MHC Class I Antigen Prolongs Liver Allograft Survival and Inhibits Recipient Anti-Donor Cytotoxic T Lymphocyte Responses", Transplantation, vol. 64, No. 5, Sep. 15, 1997, pp. 782-786.
Mitaka et al., "Multiple Cell Cycles Occur in Rat Hepatocytes Cultured in the Presence of Nicotinamide and Epidermal Growth Factor", Multiple Cell Cycles in Cultured Eat Hepatocytes, Hepatology, 1991, vol. 13, No. 1, pp. 21-30.
Tateno et al., "Heterogeneity of Growth Potential of Adult Rat Hepatocytes in Vitro", Hepatology, Jan. 2000, vol. 31, No. 1, pp. 65-74.

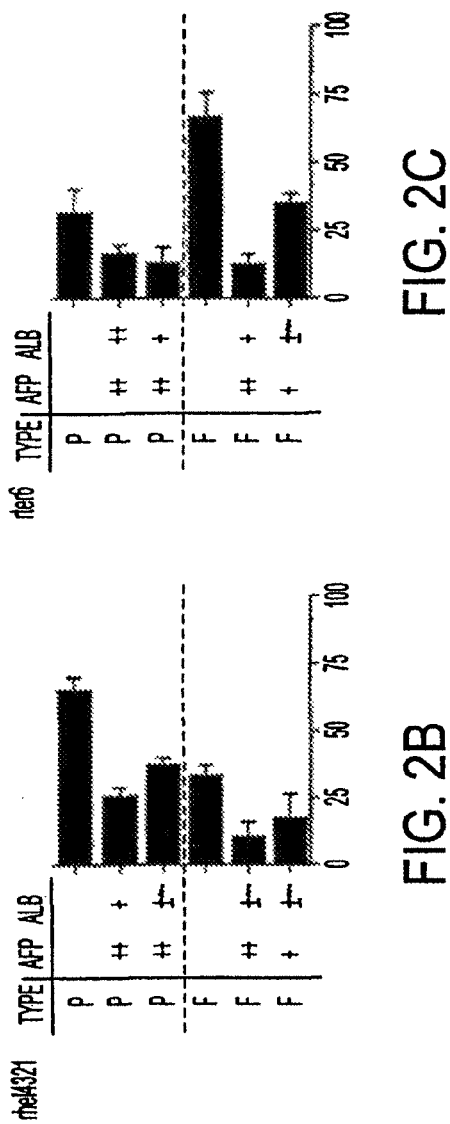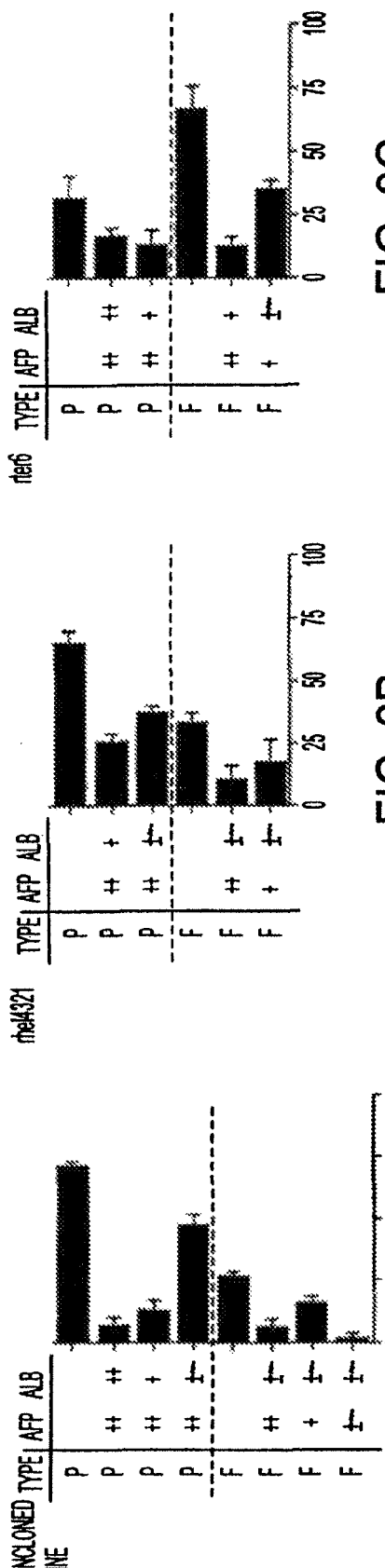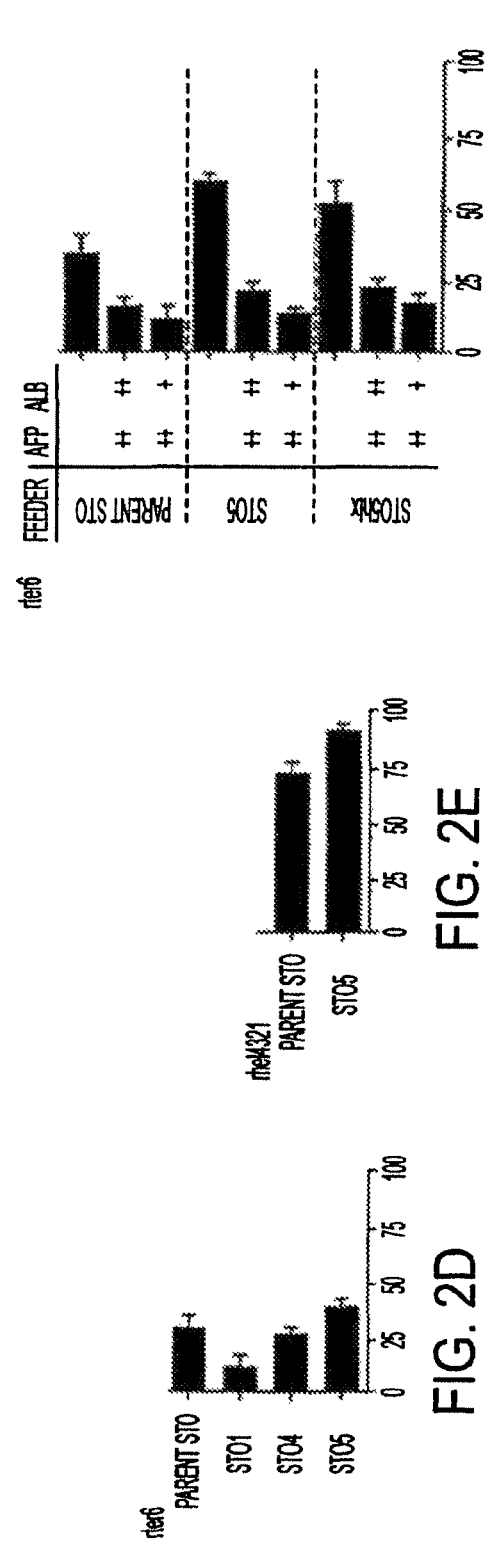
FIG. 2A FIG. 2B FIG. 2C FIG. 2D FIG. 2E FIG. 2F

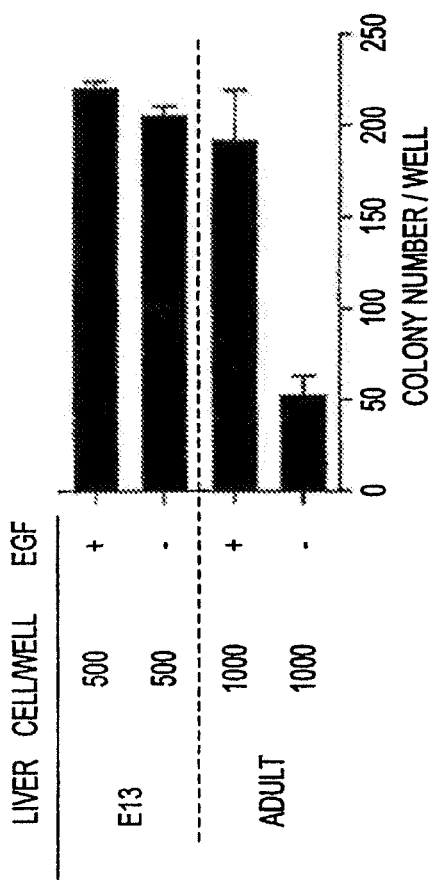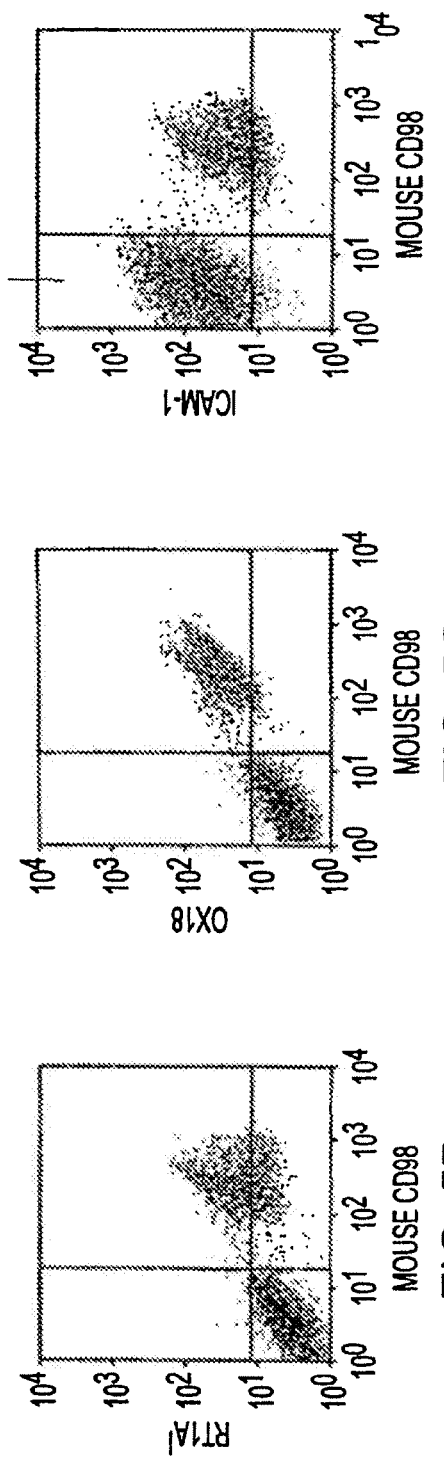

METHODS OF ISOLATING BIPOTENT HEPATIC PROGENITOR CELLS

This application is a continuation of U.S. patent application Ser. No. 11/757,168, filed on Jun. 1, 2007, which is a continuation of U.S. patent application Ser. No. 09/678,953 filed on Oct. 3, 2000, which claims priority from U.S. Provisional Application No. 60/157,052, filed on Oct. 1, 1999, all of which are incorporated herein by reference.

1. FIELD OF THE INVENTION

The present invention relates to novel cell surface markers that distinguish hepatic cells from hematopoietic cells. In particular, the invention relates to methods of isolating bipotent hepatic progenitor cells with a unique phenotype that includes cells that are negative for classical major histocompatibility complex (MHC) class I antigen, positive for the intercellular adhesion molecule 1 (ICAM-1), and dull positive for nonclassical MHC class I antigen(s). Moreover, the invention relates to the hepatic progenitor and hepatic stem cells produced by the methods of the invention.

2. DESCRIPTION OF RELATED ART

Identification of multipotential progenitor cell populations in mammalian tissues is important both for clinical and commercial interests and also for understanding of developmental processes and tissue homeostasis. Progenitor cell populations are ideal targets for gene therapy, cell transplantation and for tissue engineering of bioartificial organs (Millar, A. D. 1992 *Nature* 357, 455; Langer, R. and Vacanti, J. P. 1993 *Science* 260, 920; Gage, F. H. 1998 *Nature* 392, 18).

The existence of tissue-specific, "determined" stem cells or progenitors having high growth potential and/or pluripotentiality is readily apparent from studies on hematopoietic stem cells (Spangrude et al. 1988 *Science* 241, 58), neuronal stem cells (Davis, A. A., and Temple, S. 1994*Nature* 372, 263; Stemple, D. L., and Anderson, D. J. 1992 *Cell* 71, 973) and epidermal stem cells (Jones, P. H., and Watt, F. M. 1993 *Cell* 73, 713), each having been identified clonally by using the particular methods appropriate for that tissue. These progenitors are regarded as the cells responsible for normal hematopoietic, neuronal or epidermal tissue homeostasis and for regenerative responses after severe injury (Hall, P. A., and Watt, F. M. 1989 *Development* 106, 619).

The mammalian adult liver has a tremendous capacity to recover after either extensive hepatotoxic injury or partial hepatectomy (Fishback, F. C. 1929 *Arch. Pathol.* 7, 955); (Higgins, G. M., and Anderson, R. M. 1931 *Arch. Pathol.* 12, 186), even though the liver is usually a quiescent tissue without rapid turnover. Data from recent studies in the mouse have been interpreted to suggest that adult parenchymal cells have an almost unlimited growth potentiality as assayed by serial transplantation experiments (Overturf et al. 1997 *Am. J. Pathol.* 151, 1273); (Rhim, J. A. et al. 1994 *Science* 263, 1149). These experiments made use of heterogeneous liver cell population limiting the ability to prove that the growth potential observed derived from adult parenchymal cells, from a subpopulation of adult parenchymal cells and/or from non-parenchymal cells (i.e. progenitors). Furthermore, the studies show no evidence for biliary epithelial differentiation, since the hosts used had either albumin-urokinase transgenes or, in the other case, a tyrosine catabolic enzyme deficiency; both types of hosts have conditions that selected for the hepatocytic lineage. Therefore, the assay was incapable of testing for bipotent cell populations.

Several histological studies establish that early hepatic cells from midgestational fetuses have a developmental bipotentiality to differentiate to bile duct epithelium as well as to mature hepatocytes (Shiojiri, N. 1997 *Microscopy Res. Tech.* 39, 328-35). Hepatic development begins in the ventral foregut endoderm immediately after the endodermal epithelium interacts with the cardiogenic mesoderm (Douarin, N. M. 1975 *Medical Biol.* 53, 427); (Houssaint, E. 1980 *Cell Differ.* 9, 269). This hepatic commitment occurs at embryonic day (E) 8 in the mouse. The initial phase of hepatic development becomes evident with the induction of serum albumin and alpha-fetoprotein mRNAs in the endoderm and prior to morphological changes (Gualdi, R. et al. 1996 *Genes Dev.* 10, 1670). At E 9.5 of mouse gestation, the specified cells then proliferate and penetrate into the mesenchyme of the septum transversum with a cord-like fashion, forming the liver anlage. Although the liver mass then increases dramatically, the increase in mass is due largely to hematopoietic cells, which colonize the fetal liver at E10 in the mouse (Houssaint, E. 1981 *Cell Differ.* 10, 243) and influence the hepatic cells to show an extremely distorted and irregular shape (Luzzatto, A. C. 1981 *Cell Tissue Res.* 215, 133). Interestingly, recent data from gene-targeting mutant mice indicates that impairment of a number of genes has led to lethal hepatic failure, apoptosis and/or necrosis of parenchymal cells between E12 to E15 (Gunes, C. et al. 1998 *EMBO J.* 17, 2846; Hilberg, F. et al. 1993 *Nature* 365, 1791; Motoyama, J. et al. 1997 *Mech. Dev.* 66, 27; Schmidt, C. et al. 1995 *Nature* 373, 699). Especially gene disruptions that are part of the stress-activated cascade (Ganiatsas, S. et al. 1998. *Proc. Natl. Acad. Sci. USA* 95, 6881; Nishina, H. et al. 1999 *Development* 126, 505) or anti-apoptotic cascade (Beg, A. et al. 1995 *Nature* 376, 167; Li, Q. et al. 1999 *Science* 284, 321; Tanaka, M. et al. 1999. *Immunity* 10, 421) can result in severely impaired hepatogenesis, not hematopoiesis, in spite of the broad expression of the inactivated gene. It is not clear whether hepatic cells are intrinsically sensitive to developmental stress stimuli or that the particular microenvironment in fetal liver per se causes such destructive effects (Doi, T. S. et al 1999 *Proc. Natl. Acad. Sci. USA* 96, 2994). On the other hand, the basic architecture of adult liver is dependent on the appearance of the initial cylinder of bile duct epithelium surrounding the portal vein (Shiojiri, N. 1997 *Microscopy Res. Tech.* 39, 328). Immunohistologically, the first sign of the differentiation of intrahepatic bile duct epithelial cells is the expression of biliary-specific cytokeratin (CK). CK proteins, the cytoplasmic intermediate filament (IF) proteins of epithelial cells, are encoded by a multigene family and expressed in a tissue- and differentiation-specific manner (Moll, R. et al. 1982 *Cell* 31, 11). CK19 is one of the most remarkable biliary markers, because adult hepatocytes do not express CK19 at all, whereas adult biliary epithelial cells do express this protein. Only CK8 and CK18 are expressed through early hepatic cells to adult hepatocytes (Moll, R. et al. 1982 *Cell* 31, 11). At E15.5 in the rat development, corresponding to E14 in the mouse, the biliary precursors are heavily stained by both CK18 and CK8 antibodies, and some biliary precursors express CK19. As development progresses, maturing bile ducts gradually express CK7 in addition to CK19 and lose the expression of albumin (Shiojiri, N. et al. 1991 *Cancer Res.* 51, 2611). Although hepatic cells as early as E13 in the rat are thought to be a homogeneous population, it remains to be seen whether all early hepatic cells can differentiate to biliary epithelial cell lineage, and how their fates are determined. Definitive lineage-marking studies, such as those using retroviral vectors, have not been done for hepatic cells, and clonal culture conditions requisite for the demonstration of any bipotent hepatic progenitor cells have not been identified.

For clonal growth analyses, one major obstacle is the explosive expansion of hematopoietic cells, marring the ability to observe ex vivo expansion of hepatic cells. Therefore an enrichment process for the hepatic population must be used. Although the surface markers to be able to fractionate the hematopoietic cells in fetal liver have been investigated in detail (Dzierzak, E. et al. 1998 *Immunol. Today* 19, 228-36), those for hepatic progenitor cells are still poorly defined, since the studies are still in their infancy (Sigal, S. et al. 1994 *Hepatology* 19, 999). Furthermore, the ex vivo proliferation conditions typically used for adult liver cells result in their dedifferentiation with loss of tissue-specific functions such as albumin expression (Block, G. D. et al. 1996 *J. Cell Biol.* 132, 1133). A somewhat improved ability to synthesize tissue-specific mRNAs and ability to regulate tissue-specific genes fully post-transcriptionally occurs only in liver cells maintained in the absence of serum and with a defined mixture of hormones, growth factors and/or with certain extracellular matrix components (Jefferson, D. M. et al. 1984. *Mol. Cell. Biol.* 4, 1929; Enat R, et al 1984, 81, 1411). Proliferating fetal hepatic cells, however, maintain the expression of such serum proteins in vivo.

In addition to hepatic progenitor cells, the fetal liver in many species contains hematopoietic progenitor cells. The hematopoietic progenitor cells and hematopoietic cells express major histocompatability (MHC) antigens on their surfaces. The nomenclature of MHC has not been entirely standardized. Thus the classical MHC class I antigen may also be designated MHC class Ia or MHC class IA. Similarly, the non-classical MHC class I antigen may also be designated MHC class Ib or MHC class IB.

Among work on MHC antigens, U.S. Pat. No. 5,679,340 to Chappel claims modification of cell surface antigens including MHC by binding antibodies to two antigenic epitopes. In contrast, Chappel fails to teach that MHC and other antigens can be used for isolation of progenitor cells.

Others have attempted to grow hepatocytes in vitro. U.S. Pat. No. 5,510,254 to Naughton et al. claims the culture of hepatocytes depends on a three-dimensional framework of biocompatible but non-living material. Thus there is an unmet need for culture conditions with no artificial framework and providing the condition for hepatic progenitors to be expanded and cultured. Furthermore, there is an unmet need for methods of cloning of hepatic progenitors with biopotential differentiation capability, where the cells would be suitable for use as components of a bio-artificial liver, for testing of hepatotoxins and drug development, among other uses.

U.S. Pat. No. 5,559,022 to Naughton et al., claims liver reserve cells that bind Eosin Y, a stain that was used to characterize the "reserve cells." U.S. Pat. No. 5,559,022 does not use well-established markers for identification of liver reserve cells, nor provide methods for clonal expansion of reserve cells, nor provided markers by which to isolate viable liver reserve cells. Thus, there is an unfilled need for methods to isolate and culture cells that have many features essential to hepatic progenitors, including expression of specific markers and the potential to differentiate into either hepatocytes or biliary cells. Equally needed are methods for clonal growth of the hepatic progenitors. Clonal growth is essential as a clear and rigorous distinction and identification of pluripotent hepatic progenitors.

The present inventors have recognized the inadequacy of growing mature liver cells, such as hepatocytes, rather than the far more useful hepatic progenitors. They have carefully defined the isolation parameters for hepatic progenitors and requirements for clonal growth. The progenitor cells and the methods for selecting and culturing the progenitors have many uses, including utility in medicine for treatment of patients with liver failure, and utility for evaluation of toxicity agents, and utility for evaluation of drugs.

3. SUMMARY OF THE INVENTION

The present invention relates to a method of isolating hepatic bipotent progenitor cells where the cells do not express the classical MHC class I antigen (MHC class Ia antigen) and do express the ICAM antigen or ICAM-1 antigen. Furthermore, the hepatic bipotent progenitor can optionally express nonclassical MHC class I antigen(s) (MHC class Ib antigen) containing monomorphic epitope of MHC class I. Progenitors from several tissues can be used, including, but not limited to, liver. Thus, the invention relates to a method of isolating hepatic progenitor cells that are classical MHC class I negative and, optionally, ICAM-1 positive. Likewise, the present invention relates to a method of isolating progenitor cells, where the cells express the phenotype of ICAM-1 positive but classical MHC class I negative, by removing cells that express the phenotype classical MHC class I positive. The dull expression of nonclassical MHC class I can be used for further isolation of progenitor cells. Preferably, the invention relates to a method of isolating and cloning hepatic pluripotent progenitor cells. The hepatic pluripotent progenitor cells may be of any vertebrate species including fish, amphibian, reptilian, avian, and mammalian, and more preferably mammalian. Even more preferably, the hepatic pluripotent progenitor cells are primate, pig, rat, rabbit, dog, or mouse in origin. Most preferably the pluripotent progenitor cells are human in origin. The very most preferable method yields hepatic progenitors that are bipotent hepatic progenitors. Thus the bipotent hepatic progenitors can differentiate, or their progeny can differentiate, into either hepatocytes or biliary cells.

A cell population enriched in progenitors can be obtained by a method of first obtaining a cell suspension of vertebrate cells. Then, sequentially in either order, or substantially simultaneously, the cells that express at least one MHC class Ia antigen and those that express an ICAM antigen, are removed from the cell suspension to provide a mixture of cells enriched in progenitors. Equally, a mixture of vertebrate embryonic stem cell can be obtained that is enriched in hepatic progenitors by providing a vertebrate embryonic stem cell, expanding the embryonic stem cell to give embryonic stem cell progeny and isolating those embryonic stem cell progeny which express ICAM antigen and do not express MHC class Ia antigen.

All methods of separation by physical, immunological, and cell culture means known in the art are included in the invention. The methods of separation specifically include the immunoseparations. Immunoseparations can be flow cytometry after interaction with a labeled antibody. Immunoseparation methods also include affinity methods with antibodies bound to magnetic beads, biodegradable beads, non-biodegradable beads, to panning surfaces including dishes, and to combinations of these methods.

Furthermore, the hepatic progenitor and bipotent stem cells, and their progeny, can optionally express other phenotypes, including, but in no way limited to alpha-fetoprotein, albumin, a higher side scatter than hematopoietic cells from fetal liver, or a pattern of growth as cells that pile up.

Hepatic stem cells are cells that might or might not express alpha-fetoprotein or albumin but give rise to cells that express alpha-fetoprotein and albumin or biliary markers such as CK19.

The invention also relates to a method for the identification of progenitor cells, preferably hepatic progenitor cells, by exposing liver cells to a means of detecting a MHC class I phenotype in combination with ICAM-1 expression, and identifying those cells within the population that do not express classical MHC class I antigen. Likewise, other markers of progenitor or hepatic phenotypes such as alpha-fetoprotein can be detected.

The invention additionally relates to hepatic stem and progenitor cells, and their progeny, characterized by a phenotype of classical MHC class I negative and ICAM-1 positive, which cells can optionally express other phenotypes, including, but in no way limited to nonclassical MHC class I dull positive, a higher side scatter than hematopoietic cells progenitors, or a pattern of growth as cells that pile up. The progeny can express alpha-fetoprotein, albumin, or CK 19. The progeny of the hepatic stem and progenitor cells so isolated can retain the parental phenotype and optionally can develop and express additional phenotypes. In particular, the progeny cells can optionally express the hepatocyte phenotype and the biliary cell phenotype. Among other features, the hepatocyte phenotype is characterized by expression of albumin. Among other features, the biliary cell phenotype is characterized by expression of CK 19.

The composition of hepatic progenitors, their progeny, or a combination of the progenitors and their progeny can also comprise cells that weakly express at least on MHC class Ib antigen, exhibit a higher side scatter in flow cytometry than non-parenchymal cells, and express a polypeptide consisting of alpha-fetoprotein, albumin, CK 19, or combinations thereof. The composition can be derived from endoderm or bone marrow. In this composition, the endoderm tissue can be liver, pancreas, lung, gut, thyroid, gonad, or combinations thereof.

4. BRIEF DESCRIPTION OF THE DRAWINGS

FIG. 4A1-4D4 depicts phenotypic analysis of E13 fetal rat livers.

FIG. 5A-5D is characterization of hepatic colonies in the absence and presence of EGF.

Figure 6A:
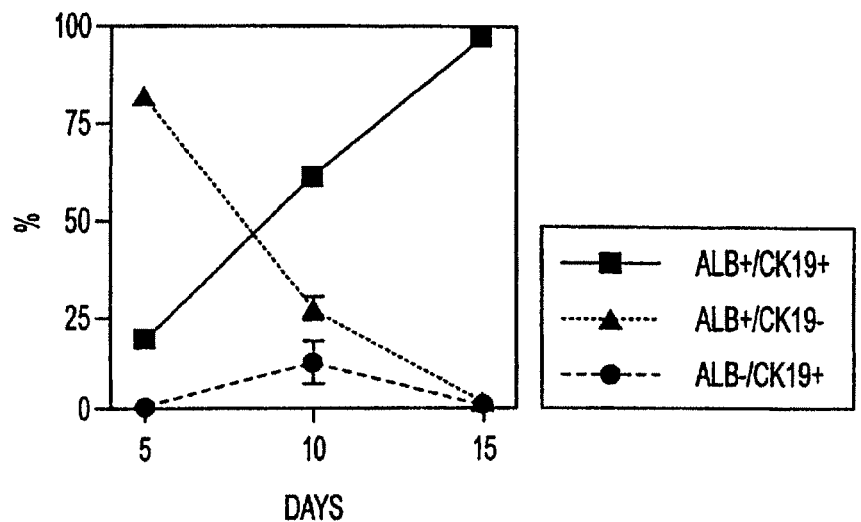
Figure 6B:
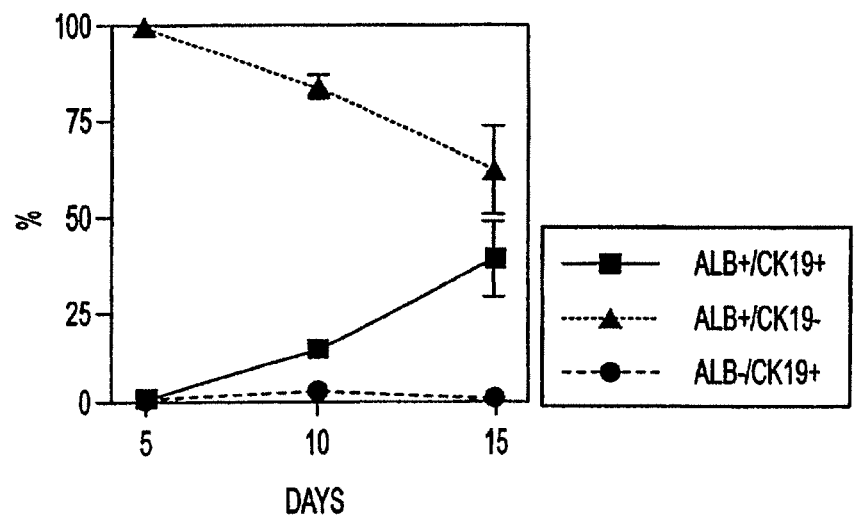

FIG. 6A-6B depicts induction of CK19 expression on RT1A$^{1-}$ hepatic cells.

Figure 7:
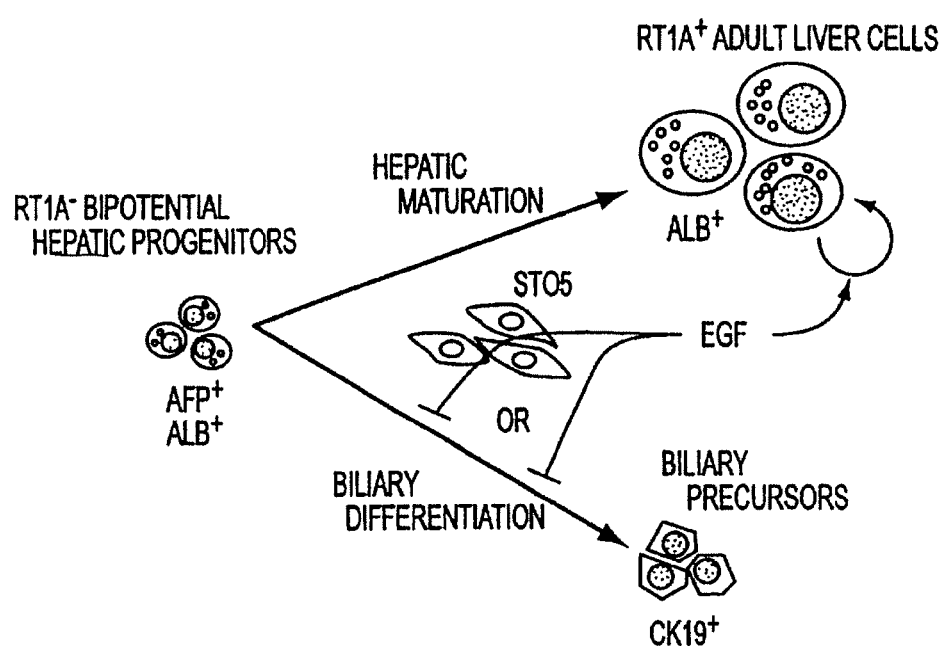

FIG. 7 is a schematic representation of hepatic colony formation on STO5 feeder cells.

5. DETAILED DESCRIPTION OF THE PREFERRED EMBODIMENTS

The instant invention is a process for isolation of progenitor cells and a composition comprising progenitor cells. In one embodiment, the invention is a process for the identification, isolation, and clonal growth of hepatic stem cells and of the hepatic progenitor cells. The process involves exposing mixed cell populations derived from an endodermal tissue such as liver to antibodies specific for an ICAM, for example ICAM-1, an adhesion protein, and classical MHC class I antigen, an antigen that characterizes hematopoietic cells and most other nucleated cells but that is substantially absent on the cell surface of hepatic stem cells and progenitors proper. The cells can be from any endodermal tissue, including but not limited to liver, pancreas, lung, gut, thyroid, gonad, or from a liver or from a whole organism. Any method of isolating hepatic stem and other early hepatic progenitor cells is acceptable, including by affinity-based interactions, e.g., affinity panning, by immunosurgery in combination with complement or with flow cytometry. The flow cytometry separation can also be based on intermediate levels of antigen expression, for example of nonclassical MHC class I antigens. In a yet more preferred embodiment, the process involves, in addition, selecting for cells that show relatively high side scatter (SSC), a parameter dependent on cellular granularity or amount of cytoplasmic lipid droplets, a feature of hepatic cells. The SSC in the hepatic progenitors is higher than in other non-parenchymal cells, such as hematopoietic cells or stromal cells in fetal liver, but lower than in mature parenchymal cells such as those in adult liver. In addition, other markers expressed on alpha-fetoprotein (AFP)-positive progenitor cells, such as CD34, CD38, CD14, and/or CD117, can be used in isolating bipotent progenitor cells. Likewise, other markers for the removal of non-hepatic progenitor cells, including, but not limited to red blood cell antigen (such as glycophorin A on red blood cells in human liver), immunoglobulin F, receptors, MHC class II antigens, ABO type markers, CD2, CD3, CD4, CD7, CD8, CD9, CD11a, CD11b, CD11c, CD15, CD16, CD19, CD20, CD28, CD32, CD36, CD42, CD43, CD45, CD56, CD57, CD61, CD74, CDw75 can be used. Furthermore, other techniques known in the art may be used as components of processes used to isolate progenitor cells, including, but not limited to: ablative techniques including laser ablation, density separation, sedimentation rate separation including zonal centrifugation, cell elutriation, selective adherence, molecular weighting including cell weighting with tetrazolium salts, size sieving, selective propagation, selective metabolic inhibition including use of cytotoxins, and multi-factor separation.

In one preferred embodiment of the invention the progenitor cells are obtained from a fetus, a child, an adolescent, or an adult.

It is a preferred embodiment of the instant invention that hepatic cells be selectively grown in a serum-free, hormone-supplemented, defined medium. It is further preferred that hepatic cells be selectively grown in culture using a layer of feeder cells, where those feeder cells are fibroblasts or another mesodermal cell derivative. It is preferred that the feeder cells are human, non-human primate, pig, rat, or mouse feeder cells, but any mammalian, avian, reptilian, amphibian, or piscine feeder cells are acceptable. It is a yet more preferred embodiment that the feeder cells be embryonic cells, although feeders from neonatal or adult tissue are acceptable. It is a yet more preferred embodiment that the feeder cells be cloned and selected for the ability to support hepatic stem and progenitor cells. It is a still more preferred embodiment of the invention that hepatic stem and progenitor cells be cultured under clonal growth conditions, thereby permitting identification as hepatic cells and expansion of a population of clonal origin.

One preferred embodiment of the invention comprises mammalian hepatic progenitor cells that are classical MHC class I negative and ICAM-1 positive. A two color sort is a convenient method to isolate the bipotent cells: ICAM-1 positive and classical MHC class I negative are two parameters to define these cells. ICAM-1 positive cell populations includes hematopoietic, mesenchymal, and mature hepatic cells. The degree of expression is quite variable depending upon the status of the cells (for example, it is different in cells in an activated or quiescent state). Classical MHC class I antigen is expressed on all nucleated hematopoietic cells from stem cells to mature cells and on mature hepatocytes (although mature hepatocytes have less expression than hematopoietic cells). In rat fetal liver, classical MHC class I negative cells include: bipotent hepatic progenitors, enucleated mature erythrocytes, and an unidentified cell population. In addition, the cells can express nonclassical MHC class I. Furthermore, the progeny of progenitors can express alpha-fetoprotein, albumin, or CK19 and can also exhibit a growth characteristic in which the cells grow in piles on top of each other, that is, in clusters.

It is an embodiment of the invention that the isolated progenitor cells have the capability to divide and produce progeny. It is further preferred that the progenitor cells are capable of more than about ten mitotic cycles. It is still more preferred that the progeny are progenitor cells or hepatocytes and biliary cells. It is a preferred embodiment of the instant invention that isolated hepatic stem and progenitor cells be committed to a hepatocyte or biliary cell lineage by the selective application of Epidermal growth factor (EGF).

In a preferred embodiment, the process involves selecting for cells that additionally express alpha-fetoprotein and bind antibody specific for alpha-fetoprotein. In another preferred embodiment, the process involves selecting for cells that, in addition, synthesize albumin and bind antibody specific for albumin.

It is a still more preferred embodiment of the instant invention that isolated stem and progenitor cells be used as a component of an extracorporeal liver. It is a further more preferred embodiment of the instant invention that the extracorporeal liver having isolated stem and progenitor cells and their progeny be used to support the life of a patient suffering from liver malfunction or failure.

The invention discloses particular culture conditions that are required for the ex vivo expansion of hepatic progenitor cells, here demonstrated from fetus. The inventors selected sublines of STO mouse embryonic cells that proved ideal as feeder cells. The feeder cells were used in combination with a novel, serum-free, hormonally defined medium (HDM). The combination enabled the inventors to establish various rat fetal hepatic cell lines from E15 liver in the rat without malignant transformation of the cells. The inventor discloses the use of the hepatic cell lines and the HDM-STO co-culture system for development of an in vitro colony forming assay (CFA) for defining clonal growth potential of hepatic progenitors freshly isolated from liver tissue. The CFA, when combined with cells sorted by a defined flow cytometric profile, reveals bipotent hepatic progenitors. For example progenitors from E13 rat livers, corresponding to E11.5 in the mouse, and with high growth potential have the phenotype as negative for classical MHC class I (RT1A region in the rat), dull positive for OX18 (monomorphic epitope on MHC class I antigens), and ICAM-1 positive. The phenotype of RT1A negative and OX18 dull positive is equivalent to nonclassical MHC class I (MHC class Ib) dull positive. EGF is disclosed in this invention to influence both growth of the progenitor colonies and their fates as either hepatocytes or biliary epithelial cells.

6. EXAMPLES

Glossary

Classical MHC class I antigen. The group of major histocompatability antigens commonly found mostly on all nucleated cells although they are most highly expressed on hematopoietic cells. The antigen is also known as MDHC class Ia. The nomenclature of the classical MHC antigens is a function of species, for example in humans the MHC antigens are termed HLA. Table 3 provides nomenclature of classical MHC antigens in several species.

Non classical MHC class I antigen. The group of major histocompatability antigens, also known as MHC class Ib, that can vary even within a species. The nomenclature of the nonclassical MHC antigens varies by species, see, e.g., Table 4.

ICAM. Intercellular adhesion molecule-1 (CD54) is a membrane glycoprotein and a member of the immunoglobulin superfamily. The ligands for ICAM-1 are the ∃2-integrin, LFA-1 (CD11a/CD18) and Mac-1 (CD11b/CD18). This molecule is also important for leukocyte attachment to endothelium. In addition ICAM-1 has a role in leukocyte extravasation. The term ICAM-1 is used to designate the form of these molecules found in mammals. The terms ICAM or ICAM-1-like are used to designate the homologous and functionally-related proteins in non-mammalian vertebrates.

Debulking. Debulking is a process of removing major cell populations from a cell suspension. In fetal liver the major non-hepatic lineage cells are red blood cells, macrophages, monocytes, granulocytes, lymphocytes, megakaryocytes, hematopoietic progenitors and stromal cells.

Dull positive. In fluorescence-activated cell sorting the intensity of emitted light is proportional to the number of fluorochrome-conjugated immunoglobulin molecules bound to the cell which, in turn, is proportional to the density of the cell surface antigen under study. As the surface density or intracellular density of antigens can vary from a few to hundreds of thousands per cell, a wide range of fluorescence intensities can be measured. The value of dull positive (or dull) is empirically determined and intermediate between the intensity of bright-fluorescing cells with many antigens and dim cells with low expression of the specified antigen. The intensity may also be defined in terms of gates or intensity intervals. The dull positive phenotype is a feature of a weakly expressed antigen. The phenotype is also described as weak or low expression.

Clonal growth. In cell culture, clonal growth is the repeated mitosis of one single initial cell to form a clone of cells derived from the one parental cell. The clone of cells can expand to form a colony or cluster of cells. Clonal growth also refers to the conditions necessary to support the viability and mitosis of a single cell. These conditions typically include an enriched and complex basal nutrient medium, an absence of serums, presence of specific growth factors and hormones, substrata of extracellular matrix of defined chemistry, and/or co-cultures of cells that supply one or more of the growth factors, hormones or matrix components.

Terms of enrichment. The term "remove" means to separate, select and set aside either to retain or discard. Thus, stromal cells can be removed from a mixed population by any of several means with the intent of either keeping them or of discarding them. The term "isolate" means to separate from a larger group and keep apart. Thus, progenitor cells can be isolated from a mixed population of progenitor and non-progenitor cells. The term "purify" means to separate away unwanted components.

Cluster growth. Hepatic progenitor cells frequently exhibit a distinctive feature, in which the cells divide and remain in mutual proximity. The progenitor cells form clusters in which cells are piled up one on another. Cells in the three-dimensional mass of piled-up cells are adjacent to feeder cells or to other progenitor cells. The clusters are also termed P-colonies or P-type colonies and are distinct from cell monolayers.

The following examples are illustrative of the invention, but the invention is by no means limited to these specific examples. The person of ordinary skill in the art will find in these examples the means to implement the instant invention. Furthermore, the person of ordinary skill in the art will recognize a multitude of alternate embodiments that fall within the scope of the present invention.

6.1. Preparation and Analysis of Hepatic Stem and Hepatic Progenitor Cells

Rats. Pregnant Fisher 344 rats are obtained from Charles River Breeding Laboratory (Wilmington, Mass.). For timed pregnancies, animals are put together in the afternoon, and the morning on which the plug is observed is designated day 0. Male Fisher 344 rats (200-250 g) are used for adult liver cells.

Establishment of hepatic cell lines from embryonic day 15 livers. Fetal livers are prepared from day 15 of the gestation. Single cell suspensions are obtained by incubating the livers with 0.05% trypsin and 0.5 mM EDTA or 10 units/ml thermolysin (Sigma, St. Louis, Mo.) and 100 units/ml deoxyribonuclease I (Sigma) for at 37° C. The cells are overlayed on Ficoll-paque (Pharmacia Biotech, Uppsala, Sweden) for gradient density centrifugation at 450 g for 15 min. The cells from the bottom fraction are inoculated into tissue culture dishes coated with 17 mg/ml collagen type IV (Collaborative Biomedical Products, Bedford, Mass.) or 12 µg/ml laminin (Collaborative Biomedical Products) for th1 120-3 and rter6 or rhe14321, respectively. The serum-free hormonally defined culture medium, HDM, is a 1:1 mixture of Dulbecco's modified Eagle's medium and Ham's F12 (DMEM/F12, GIBCO/BRL, Grand Island, N.Y.), to which is added 20 ng/ml EGF (Collaborative Biomedical Products), 5 µg/ml insulin (Sigma), $10^{-7}$M Dexamethasone (Sigma), 10 µg/ml iron-saturated transferrin (Sigma), $4.4 \times 10^{-3}$M nicotinamide (Sigma), 0.2% Bovine Serum Albumin (Sigma), $5 \times 10^{-5}$M 2-mercaptoethanol (Sigma), 7.6 µeq/l free fatty acid, $2 \times 10^{-3}$M glutamine (GIBCO/BRL), $1 \times 10^{-6}$M CuSO4, $3 \times 10^{-8}$M H2SeO3 and antibiotics. Each concentration given is the final concentration in the medium. After 4 weeks of culture, trypsinized cells are cultured on a feeder layer of mitomycin C-treated STO mouse embryonic fibroblast line (American Type Culture Collection, Rockville Md.). Th1 120-3, rter6, and rhe14321 are cloned from three independent preparations of fetal hepatic cells and are maintained on STO feeder cells with HDM. After the establishment of the cell lines, the concentration of EGF is reduced to 10 ng/ml for all cell cultures.

Dissociation of E13 of fetal liver. Fetal livers are dissected into ice-cold Ca++ free HBSS with 10 mM HEPES, 0.8 mM MgSO4 and 1 mM EGTA (pH7.4). The livers are triturated with 0.2% type IV collagenase (Sigma) and 16.5 units/ml thermolysin (Sigma) in HBSS prepared with 10 mM HEPES, 0.8 mM MgSO4, and 1 mM CaCl2. After incubation at 37° C. for 10 min, the cell suspension is digested with 0.025% trypsin and 2.5 mM EDTA (Sigma) for 10 min. Trypsin is then quenched by addition of 1 mg/ml trypsin inhibitor (Sigma). Finally, the cells are treated with 200 units/ml deoxyribonuclease I (Sigma). In all experiments, $3-5 \times 10^5$ cells per liver are obtained.

Isolation of adult liver cells. The two step liver perfusion method is performed to isolate liver cells. After perfusion, the cells are centrifuged for 1 min at 50 g twice to enrich for large parenchymal cells. Cellular viability is >90% as measured by trypan blue exclusion.

Cell adhesion assay. Adhesion of cells to fibronectin (Collaborative Biomedical Products), laminin and collagen type IV is evaluated using 96 well micro-titer plates (Corning, Cambridge, Mass.) coated with these proteins at 0.3 to 10 g/ml. After removing the STO cells by Percoll (Pharmacia Biotech) gradient density centrifugation at 200 g for 15 min, $3 \times 10^4$ cells of the hepatic cell lines, th1 120-3, rter6, and rhe14321, are cultured in each well for 10 hours with HDM. After rinsing twice to remove floating cells, fresh medium with the tetrazolium salt WST-1 (Boehringer Mannheim, Indianapolis, Ind.) is added to measure the number of variable adherent cells. After 4 hours, the absorbance is determined according to the manufacturer's protocol.

STO Sublines. One hundred cells of parent STO from ATCC are cultured in 100 mm culture dishes for 7 days in DMEM/F12 supplemented with 10% heat-inactivated fetal bovine serum, $2 \times 10^{-3}$M glutamine, $5 \times 10^{-5}$M 2-mercaptoethanol and antibiotics. Four subclones are selected for further characterization according to the cell morphology and the growth speed. Although CFA for rter6 is performed in the four subclones, one of them, STO6, does not persist in attaching to culture plates after mitomycin C-treatment. One subclone, STO5, is transfected with pEF-H1x-MC1neo or pEF-MC1neo kindly provided from Dr. J. M. Adams, The Walter and Eliza Hall. Institute of Medical Research. Linearized plasmids at Nde I site are introduced into cells by DOSPER liposomal transfection reagent (Boehringer Mannheim). After G418 selection, six clones are isolated. Three clones of each are analyzed by CFA.

Immunohistochemical Staining of Colonies. Culture plates are fixed in methanol-acetone (1:1) for 2 min at room temperature, rinsed and blocked by Hanks Balanced Salt Solution (HBSS) with 20% goat serum (GIBCO/BRL) at 4° C. For double immunohistochemistry of alpha-fetoprotein and albumin, plates are incubated with anti-rat albumin antibody (ICN Biomedicals, Costa Mesa, Calif.) followed by Texas Red-conjugated anti-rabbit IgG (Vector laboratories, Burlingame, Calif.) and FITC-conjugated anti rat alpha-fetoprotein polyclonal antibody (Nordic Immunology, Tilburg, Netherlands). For double labeling of albumin and CK19, anti-CK19 monoclonal antibody (Amersham, Buckinghamshire, England) and FITC-conjugated anti mouse IgG (Caltag, Burlingame, Calif.) are used instead of anti alpha-fetoprotein antibody.

Flow cytometric analysis. Cells are analyzed on a FACScan (Becton-Dickinson, Mountain View, Calif.) and sorted using a Moflow Flow Cytometer (Cytomation, Fort Collins, Colo.). The cell suspensions from E13 fetal liver are incubated with HBSS, containing 20% goat serum (GIBCO/BRL) and 1% teleostean gelatin (Sigma), on ice to prevent nonspecific antibody binding. After rinsing, the cells are resuspended with FITC-conjugated anti rat RT1Aa,b,1 antibody B5 (Pharmingen, San Diego, Calif.) and PE-conjugated anti-rat ICAM-1 antibody 1A29 (Pharmingen). In some experiments the cells are stained with biotinylated anti-rat monomorphic MHC class I antibody OX18 (Pharmingen) followed by a second staining with streptavidin-red670 (GIBCO/BRL) for 3 color staining. All stainings are performed with ice-cold Ca++ free HBSS containing 10 mM HEPES, 0.8 mM MgSO4, 0.2 mM EGTA, and 0.2% BSA (pH 7.4). The established three hepatic cell lines are trypsinized and fractionated by Percoll density gradient centrifugation to remove feeder cells. The rat hepatoma cell line, FTO-2B, and the rat liver epithelial cell line, WB-F344, as well as adult liver cells are stained to compare with the fetal hepatic cell lines. The cell lines are kind gifts of Dr. R. E. K. Fournier, Fred Hutchinson Cancer Research Center, Seattle, Wash., and Dr. M.-S. Tsao, University of North Carolina, Chapel Hill, N.C., respectively. Cells are blocked and stained with FITC-conjugated B5, OX18, PE-conjugated 1A29 or anti FITC-conjugated rat integrin □1 antibody Ha2/5 (Pharmingen). FITC-conjugated anti mouse IgG is used for OX18. Cell suspensions of three fetal hepatic cell lines are stained with biotinylated anti-mouse CD98 followed by a second staining with streptavidin-red670 as well as anti-rat moAb to gate out mouse cell populations.

CFA for hepatic cell lines, sorted cells, and adult liver cells. The hepatic cell lines are plated in triplicate at 500 cells per 9.6 cm2 on mitomycin C-treated STO feeder layer with the same HDM as used for maintaining each cell line. Before plating, cell are trypsinized and fractionated by Percoll density gradient centrifugation to remove feeder cells. The cultures are incubated for 10 to 14 days with medium changes every other day. Double immunofluorescence staining of alpha-fetoprotein and albumin is then performed. 100 colonies per well are analyzed by the colony morphology, P or F type, and the expression of alpha-fetoprotein and albumin. The colonies are stained using Diff-Quick (Baxter, McGaw Park, Ill.) to count the number of the colonies per well. In the CFA for primary sorted cells and adult liver cells, the plating cell number is changed as described. As another minor modification, the culture period is expanded to between 14 and 17 days, and the concentration of dexamethasone is increased to 10-6M. All other procedures are performed as above. In the CFA for adult liver cells, small numbers of clumps of liver cells are not eliminated from the cell suspension after the preparation. Therefore, an undefined number of the colonies might be produced from the clumps. For CFA of biliary differentiation on sorted cells, double immunofluorescence staining of albumin and CK19 of the colonies is performed at 5 days each of the culture in the presence or absence of EGF. At day 5 of the cultures, any colony with more than one CK19+ cell is counted as a CK19+ colony. At day 10 and 15, colonies containing multiple clusters of two CK19+ cells or one cluster of more than three CK19+ cells are counted as a CK19+ colony. About 100 colonies per well are counted. Each point represents the mean±SD from triplicate-stained cultures.

6.2. Generation and Characterization of Fetal Rat Hepatic Cell Lines Using Feeders of Mouse Embryonic Cells with a Hormonally Defined Medium.

Simple long-term cultures of rat E15 hepatic cells are attempted to see how long fetal hepatic cells could be maintained and expanded ex vivo to produce progeny. After a gradient density centrifugation to remove hematopoietic mononuclear cells, the fetal liver cells are cultured on culture dishes coated by collagen type IV or laminin and in HDM (see example 6.1). The cells survive well for more than 4 weeks. However, secondary cultures on fresh collagen type IV- or laminin-coated dishes do not permit further expansion. When mitomycin C-treated STO embryonic mouse fibroblast cell lines are used as a feeder layer for the secondary cultures, many aggregates of cells grow. Eventually several stable hepatic cell lines are established from four independent experiments.

Figure 1A:
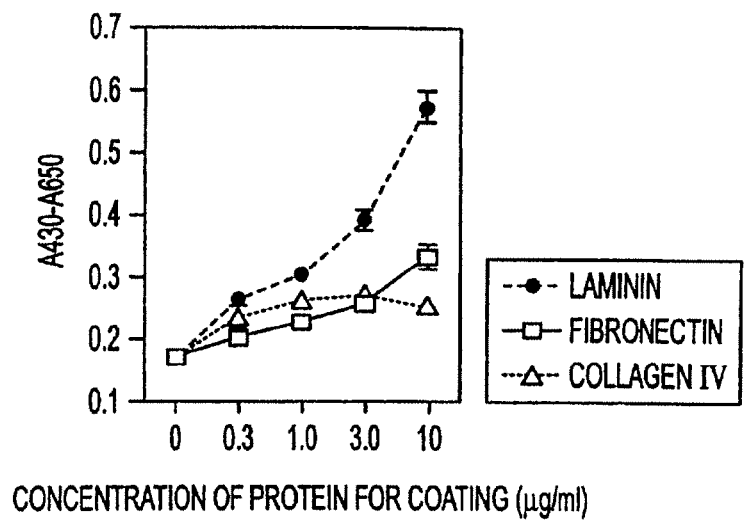
FIG. 1A-1C is a characterization of hepatic cell lines from day 15 fetal rat liver.
Figure 1B:
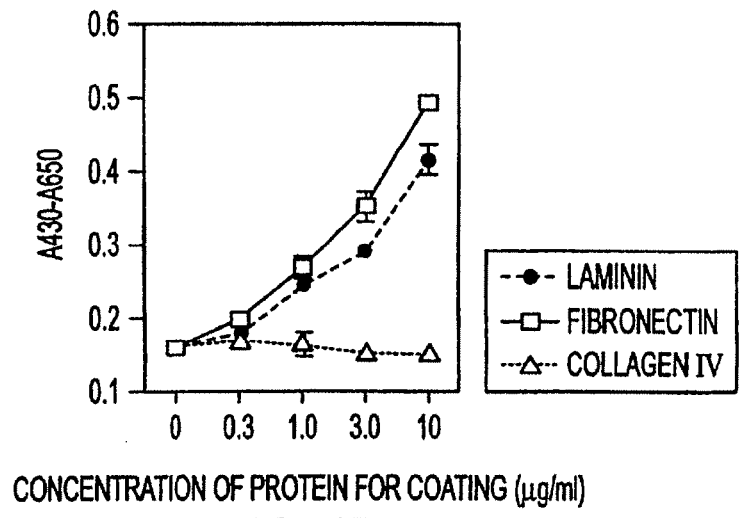
Figure 1C:
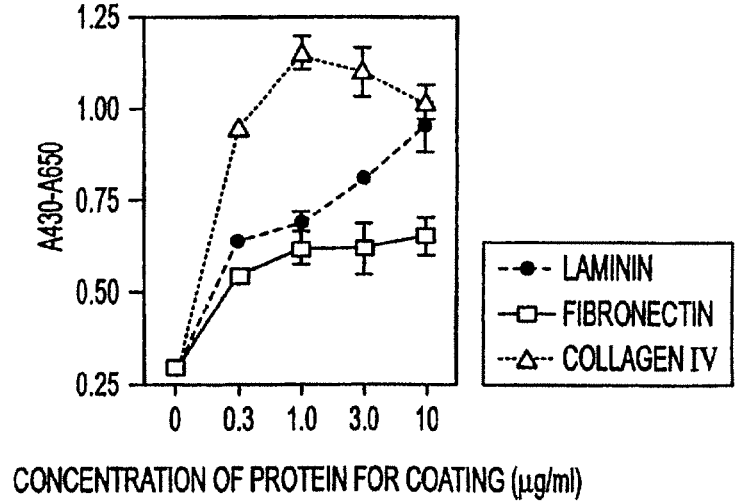

Immunohistochemical analysis of alpha-fetoprotein and albumin are performed in the continuous growing cell populations before cloning of the cell lines. Both proteins, alpha-fetoprotein and albumin, are used as the markers to confirm that cell populations originated from the hepatic lineage. A cell population with a tendency to form piles of cells, called P-colonies, had intense expression of alpha-fetoprotein and albumin, while another cluster produced flattened monolayers, called F-colonies, with diminished expression of alpha-fetoprotein and no albumin. The embryonic mouse fibroblasts, STO, do not show any reactivity to either antibody. For further analysis, three cloned hepatic cell lines from independent experiments are selected by the morphological criteria of either P type or F type colonies (FIG. 1A-1C). Rhe14321 (FIG. 1A) consists mostly of packed small cells, P type colonies, whereas th1 120-3 (FIG. 1C) makes only a flattened monolayer of F-type colonies. Rter6 (FIG. 1B) is an intermediate phenotype of these two. Interestingly, the heterogeneity of rter6 is still observed after three rounds of sequential cloning of the flattened colony. To see the heterogeneity of colonies derived from single cells in rhe14321 and rter6, the cells are cultured on STO fibroblasts for 10 to 14 days at a seeding density of 500 cells per 9.6 cm$^2$ (one well of a 6-well plate). The colonies are then characterized in terms of their morphology and their expression of alpha-fetoprotein and albumin. FIG. 2A-2F shows the results. In the cell lines, rhe14321 (FIG. 2B) and rter6 (FIG. 2C), and in the original cell population prior to cloning (FIG. 2A), almost all P-type colonies strongly express alpha-fetoprotein, whereas F-type colonies of cells do not. Furthermore, the intense expression of both alpha-fetoprotein and albumin is observed only in P type colonies. The morphological difference in the cloned hepatic cell lines correlate to the percentage of the P type colony (FIG. 2B and 2C). The percentage of P type colonies in CFA of rter6 and rhe14321 is 33.3% (±8.6% SD) and 65.7% (±4.0% SD), respectively. The total colony number per well is counted to calculate the clonal growth efficiency (colony efficiency). The efficiency of rter6 and rhe14321 is 45.7% (±1.3% SD) and 36.4% (±1.1% SD), respectively. The th1 120-3 cells tightly attach to each other along their lateral borders making preparation of single cell suspensions difficult. However, the th1 120-3 cells do not produce piled up clusters (FIG. 1C).

Next, the preferences of each of the cell lines to adhere to specific components of extracellular matrices (ECM) are tested, because the adhesion of mouse liver cells to such ECM proteins as laminin, collagen type IV, and fibronectin, changes in different developmental stages. Whereas collagen type IV is the most effective in the attachment of the 1 120-3 (FIG. 1C), similar to the findings for the adult liver cells, it works less well for rter6 (FIG. 1B) and rhe14321 (FIG. 1A). Laminin is the most effective substratum for adhesion of rhe14321 (FIG. 1A). This preference is similar to that of primary cultures of mouse fetal liver cells (Hirata et al., 1983). In summary, the conserved expression of alpha-fetoprotein and albumin in P-type colonies and preferential adherence to laminin by rhe14321, suggest that the cell populations producing P type colonies are more strictly associated with hepatic progenitor cells.

6.3. Isolation of STO Subclones for the Colony Formation; Assay of Hepatic Progenitors To develop a CFA system to identify bipotent hepatic progenitors with high growth potential, the culture system has to be able to support cell expansion at clonal seeding densities and with conservation of critical original hepatic functions. Albumin and alpha-fetoprotein are two of the most significant markers for early hepatic development. The culture conditions optimizing P type colonies should be the best, since P type, but not F type, colonies maintain the expression of alpha-fetoprotein and albumin during clonal expansion. Therefore, STO subclones are compared in their support of P type colonies of rter6. One of the clones, STO5, supports the P type colony formation more than any of the other sublines and more than the parent line (FIG. 2D). The CFA of rhe14321 also confirms that STO5 is a more effective feeder than the parent STO (FIG. 2E). The mouse Hlx gene product, expressed in the mesenchymal cells lining digestive tract from E10.5, is essential for fetal hepatic cell expansion. Although the mRNA expression for the Hlx gene is analyzed in all the STO subclones, there is no significant difference in its expression among the subclones (data not shown). Furthermore, the stable transfectants of mouse Hlx in STO5 do not result in an improvement in the colony formation assays (FIG. 2F). One clone of the transfectants, however, is used for further experiments, because the transfectant supports a more stable persistence of the original morphology of STO5 at relatively high passages.

6.4. Identification of Hepatic Progenitors from E13 Fetal Liver Using the Surface Antigenic Markers and the Colony Forming Assay.

Figure 3A:
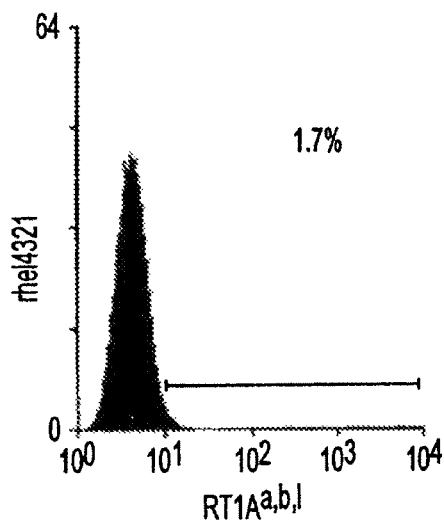
FIG. 3A-3X is an expression of rat cell surface antigens on various hepatic cell lines in adult liver cells.
Figure 3B:
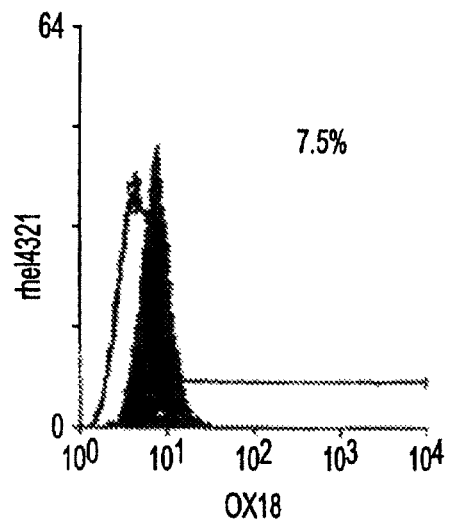
Figure 3C:
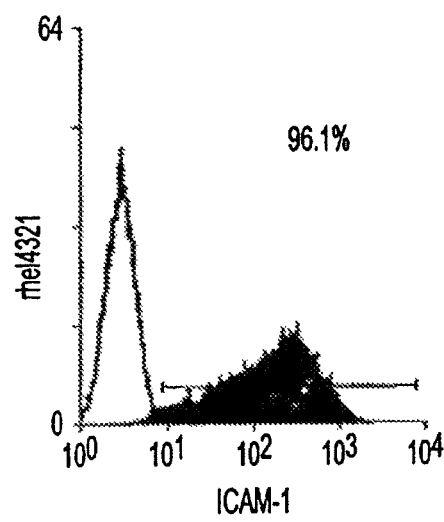
Figure 3D:
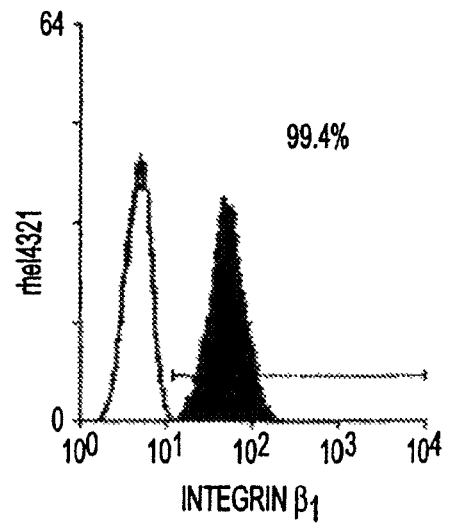
Figure 3E:
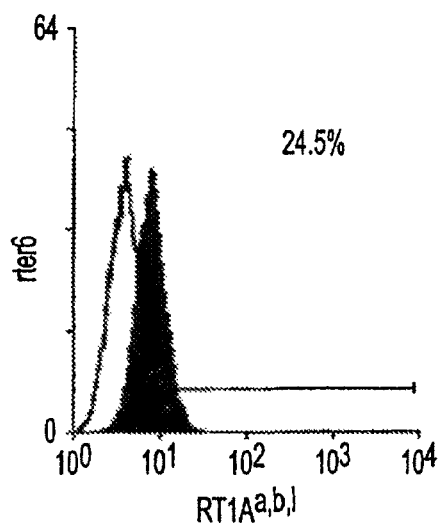
Figure 3F:
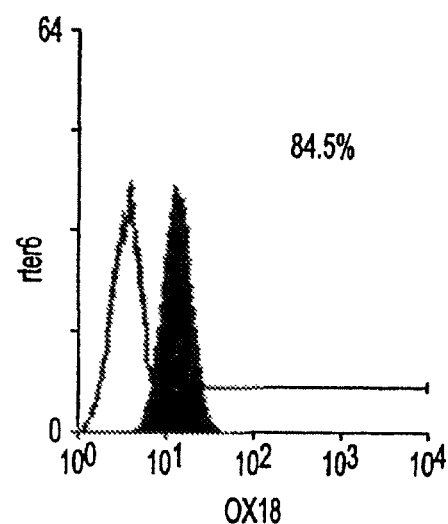
Figure 3G:
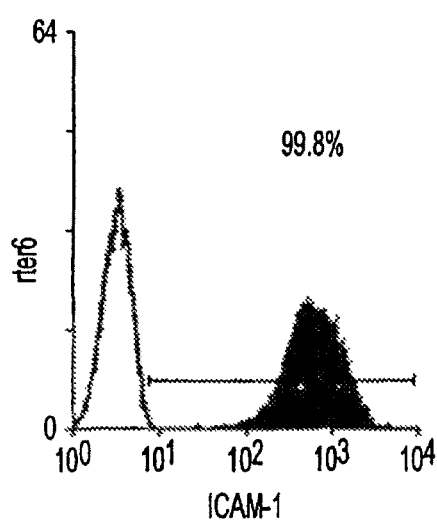
Figure 3H:
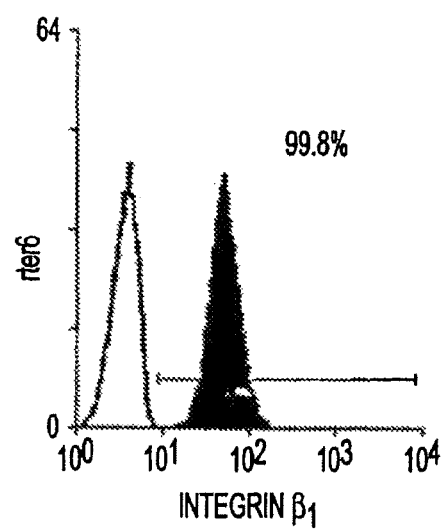
Figure 3I:
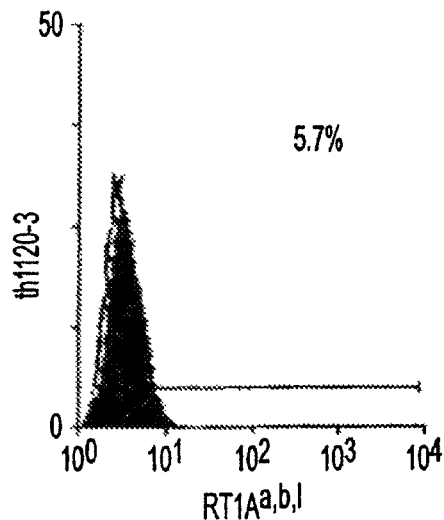
Figure 3J:
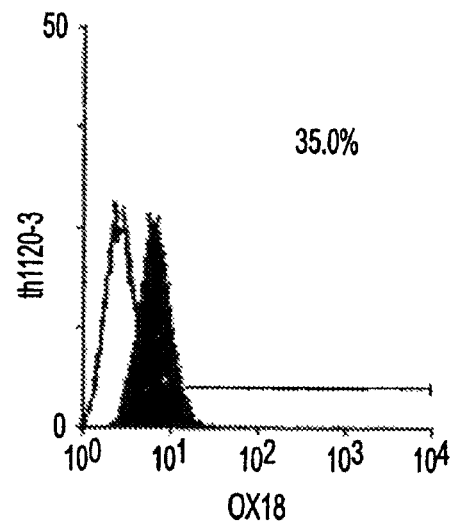
Figure 3K:
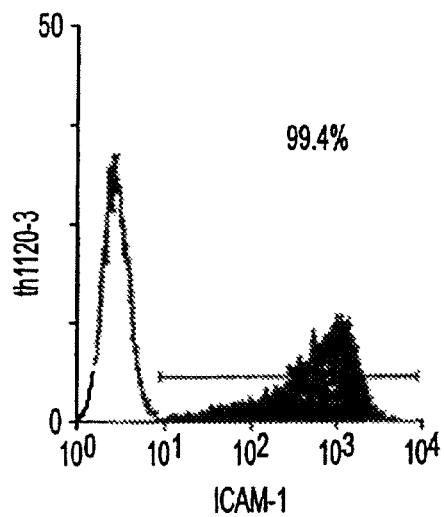
Figure 3L:
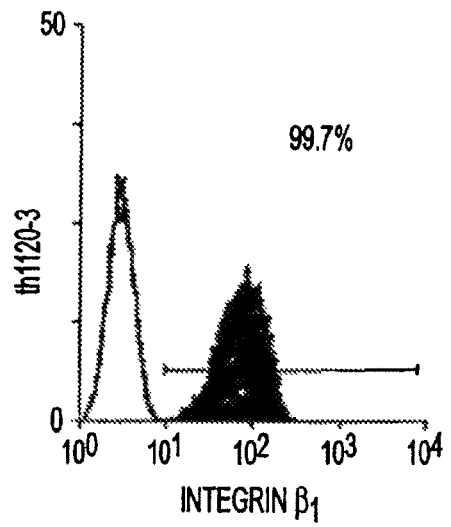
Figure 3M:
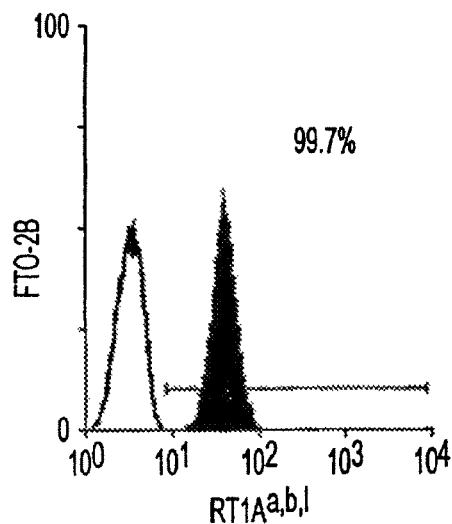
Figure 3N:
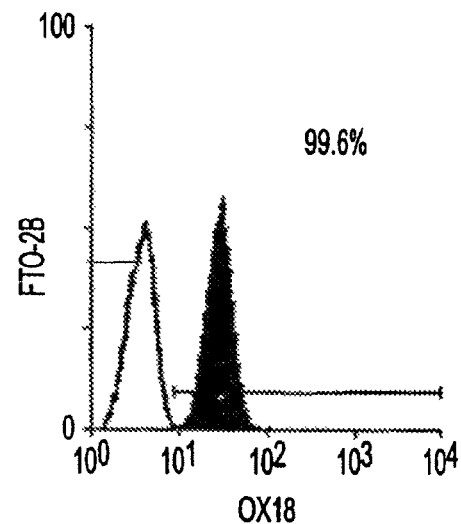
Figure 3O:
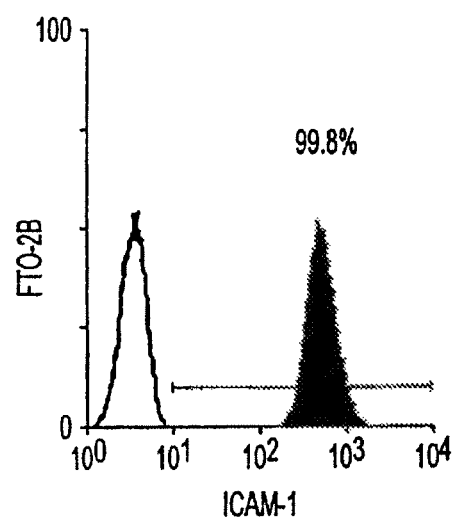
Figure 3P:
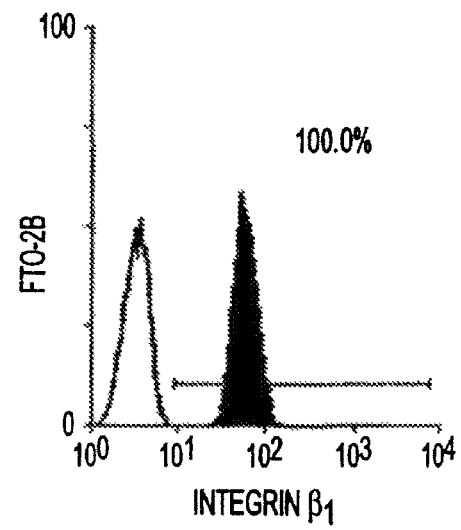
Figure 3Q:
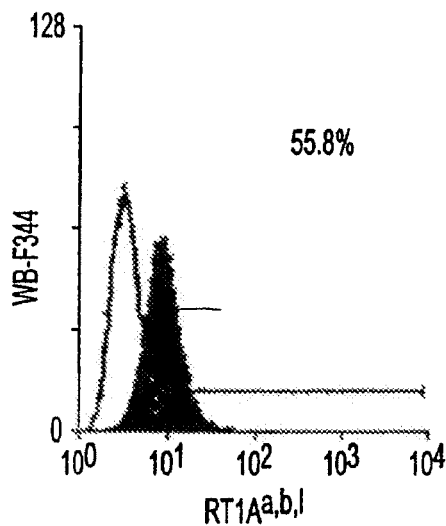
Figure 3R:
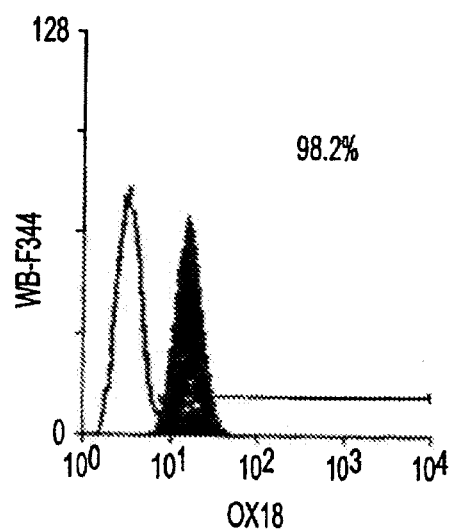
Figure 3S:
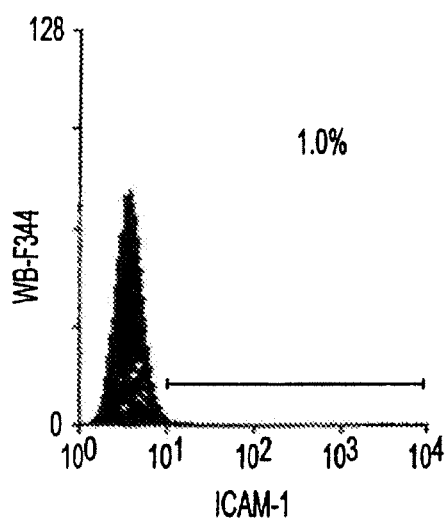
Figure 3T:
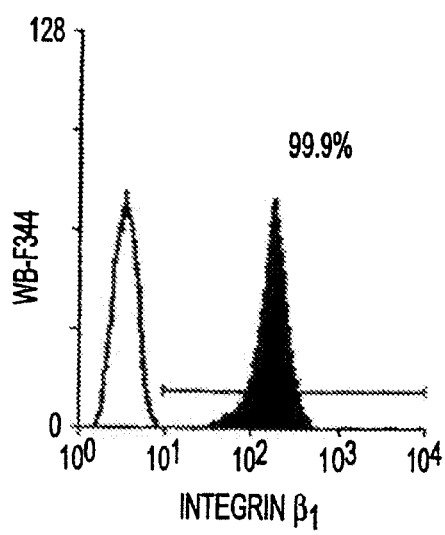
Figure 3U:
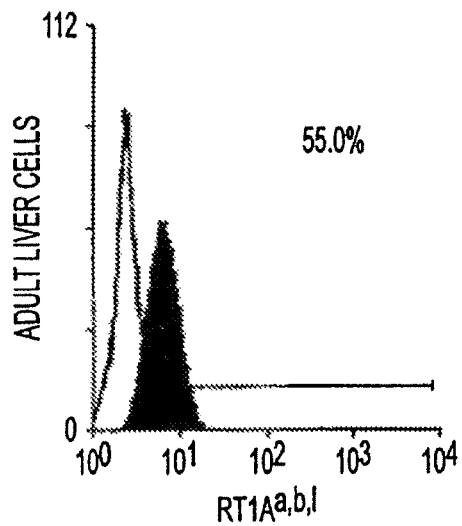
Figure 3V:
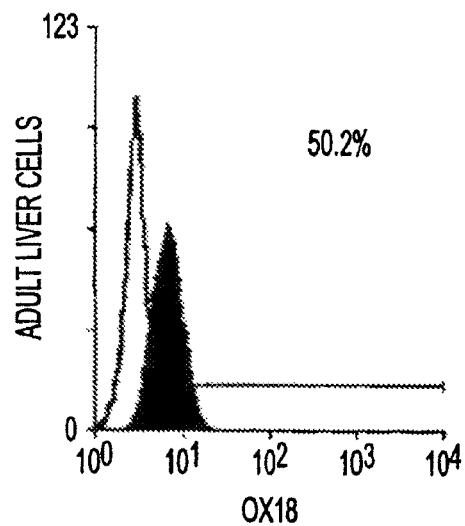
Figure 3W:
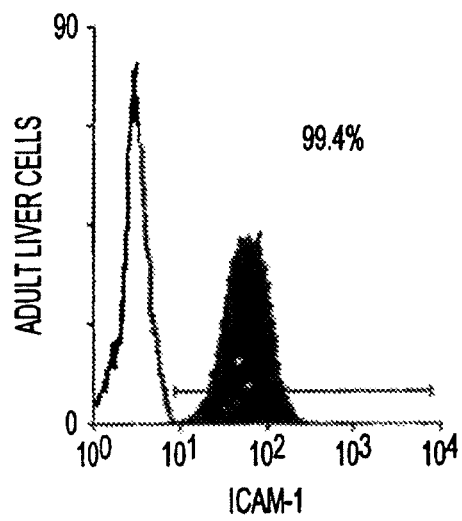
Figure 3X:
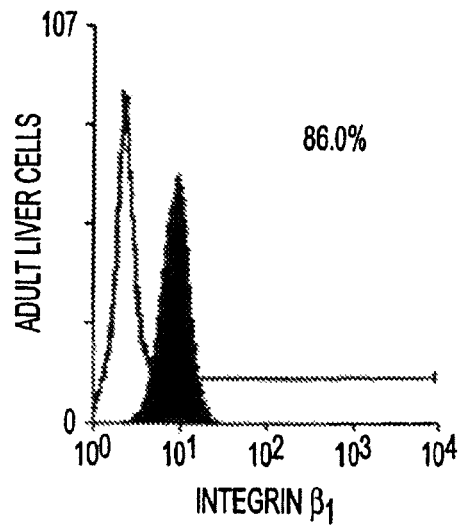
Figures 1, 4A:
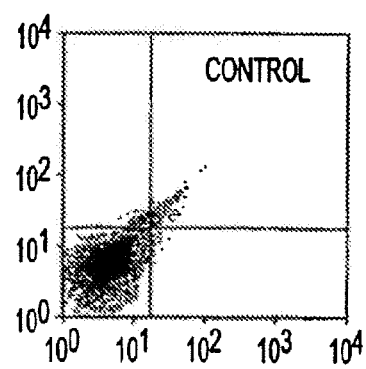
Figures 2, 4A:
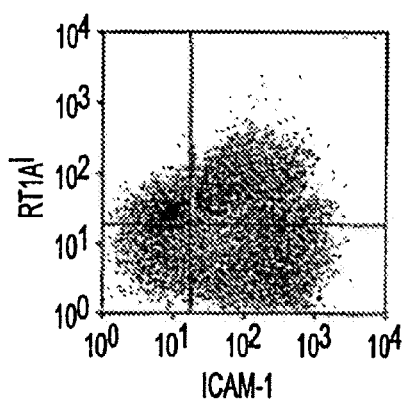
FIG. 2A-2F is an assay of colony formation on feeder cells.
Figures 1, 4B:
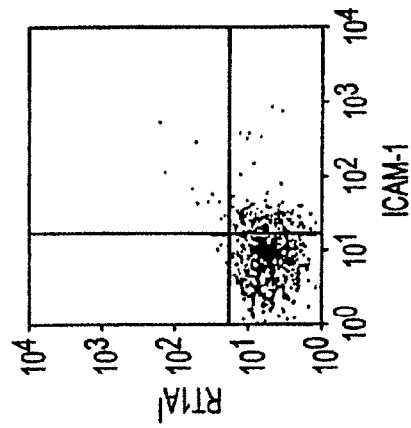
Figures 2, 4B:
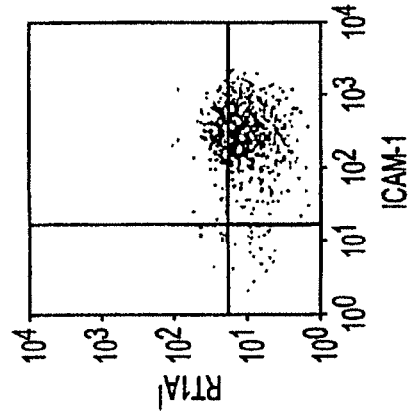

Hepatopoiesis and massive amounts of hematopoiesis coexist in the fetal liver. So far, the antigenic profile of hematopoietic progenitors has extensively been analyzed, whereas studies of early hepatic progenitors are still in their infancy. The antigenic profile of hepatic cells is analyzed using the three hepatic cell lines established in this study, an adult hepatocarcinoma cell line (FTO-2B), an epithelial cell line from adult rat liver (WB-F344), and freshly isolated adult liver cells (FIG. 3A-3X). Compared with FTO-2B, WB-F344, and adult liver cells, the pattern of the most immature of the fetal hepatic cell lines, rhe14321, is quite unique in that there is no expression of classical MHC class I ($RT1A^1$) (FIG. 3A). The cell line th1 120-3 is similar to rhe14321 in the pattern of $RT1A^1$ (FIG. 3I), OX18 (pan-MHC class I) (FIG. 3J), and ICAM-1 (FIG. 3K), whereas rter6 has relatively high expression of $RT1A^1$ (FIG. 3E) and OX18 (FIG. 3F). Additionally, another cell line from a different experiment, which has an identical morphology to rhe14321 (FIG. 1A-1C), is also $RT1A^{1-}$, $OX18^{dull}$, and $ICAM-1^+$. Integrin $b_1$ expression is similar in all the cell lines, while the pattern of $RT1A^{a,b,1}$ and ICAM-1 is unique among them. The antigenic profile of adult liver cells is $RT1A^{1+}$ (FIG. 3U), $OX18^+$ (FIG. 3V), and $ICAM-1^+$ (FIG. 3W). Since, in the adult rat, all bone marrow cells except mature erythrocytes strongly express MHC class I molecules, the fetal hepatic population can be separated from the hemopoietic cell populations by MHC class I expression. The cell suspensions from rat E13 livers are stained with anti $RT1A^1$ and ICAM-1 antibodies. FIG. 4A1 to 4A2 shows the 2 color-staining pattern of $RT1A^1$ and ICAM-1. To determine which fraction contains the hepatic cell population, five fractions (FIG. 4B-1 to 4B-5) are isolated by fluorescent activated cell sorting and then screened by CFA for clonal growth potential. FIG. 4B-1 to 4B-5 represents the result of resorting of the five fractions after sorting. The hepatic cell colonies, defined by expression of albumin and alpha-fetoprotein, are distinguishable also morphologically, enabling one to count the number of hepatic colonies per well. The majority of the hepatic colonies are detected in the gate $RT1A^{1dull}$ and $ICAM-I^+$ (Table 1, FIG. 4B-2, i.e. gate 2), and the frequency of the P type colony is 75.6% (±4.9% SD). Gate 1 (FIG. 4B-1) shows a much lower number of the colonies, and the other fractions contain negligible numbers of cells with colony forming ability. In gates 1 and 2, the expression of both alpha-fetoprotein and albumin is confirmed in all the hepatic colonies. Some of the colonies, derived from cells in gate 2, are larger than others. To investigate the MHC class I expression on the hepatic cells in detail, three color staining of $RT1A^{1-}$, ICAM-1, and OX18 with the sidescatter (SSC) as another parameter is used for the cell fractionation. Sidescatter (SSC), a reflection of the granularity of cell, is a useful parameter for separation of hepatic from hematopoietic cells, because fetal hepatic cells contain lipid droplets as early as E11 of gestation. FIG. 4C-1 to 4C-5 shows that the gate 2 contains the highest number of colony-forming cells. Gating R2 based on the SSC, the population corresponding to the gate 2 clearly shows $RT1A^{1-}$ and $OX18^{dull}$ phenotype (FIG. 4C-1 to 4C-5 and FIG. 4D-1 to 4D-4). The CFA confirms that R4 harbors more colony-forming cells than gate 2 (Table 1). These results suggest that most of the $RT1A^{1-}$, $OX18^{dull}$, and $ICAM-1^+$ population from E13 rat liver are hepatic cells producing alpha-fetoprotein$^+$ and albumin$^+$ colonies. It is the identical antigenic profile found for rhe14321 cells (FIG. 3A to 3D).

TABLE 1

The Frequency of hepatic colonies from sorted E13 fetal liver based on the expression of RT1A and ICAM-1.

| Gate | Inoculated cell (per well) | Hepatic colony (per well) | Efficiency of colony formation (%) |
|---|---|---|---|
| 1 | 1000 | 8.7 ± 4.0 | 0.87 |
| 2 | 500 | 136.3 ± 4.6 | 27 |
| 3 | 5000 | 10.0 ± 7.9 | 0.13 |
| 4 | 5000 | 6.3 ± 0.6 | 0.13 |
| 5 | 5000 | 5.0 ± 1.0 | 0.10 |
| R3 | 1000 | 7.0 ± 2.6 | 0.70 |
| R4 | 500 | 269.3 ± 9.8 | 54 |

Colony forming culture on STO5hlx containing indicated cell number from each fraction of E13 of fetal liver. Number of the hepatic colonies was established from triplicate stained cultures (mean±SD). Efficiency of the colony formation express the percentage of cells inoculated to culture that went on to form colonies analyzed after 16 days of the culture.

6.5. Different Growth Requirement of E13 Hepatic Cells and Adult Liver Cells

Figures 3, 4B:
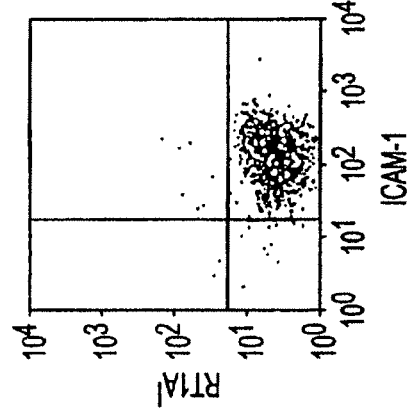

The growth requirement of the sorted hepatic cells from E13 liver are studied using the defined STO5 feeders and the HDM. EGF has long been known as a potent growth factor for adult liver cells. Therefore, the effects of EGF for colony formation of sorted hepatic cells are investigated. The colony-size of the $RT1A^{1-}$ $OX18^{dull}$, $ICAM-1^+$ hepatic cells becomes bigger in the absence of EGF, whereas adult liver cells yielded colonies only in the presence of EGF (FIG. 5A). Furthermore, the morphology of the colonies derived from adult liver cells is the typical F type, whereas all $RT1A^{1-}$ hepatic cells produce P type colonies without EGF. However, the colony efficiency is reduced slightly by the absence of EGF (FIG. 6A). Interestingly, the culture condition in the absence of EGF emphasized the two types of P-colonies, P1 and P2. Although the majority of the colonies is P2 type, at the 12th day of culture, it is difficult to distinguish the two types definitively because some of them do not have the typical morphology. These results suggest that fetal hepatic cells and adult liver cells are intrinsically different in their growth requirement as well as in their expression of $RT1A^1$ (FIGS. 3 and 4) and colony morphology.

After 3 weeks of culture, when growth seems to reach a maximum, the expression of $RT1A^{1-}$, OX18, and ICAM-1 is assessed. As shown in FIG. 5B to 5D, the expression of $RT1A^1$ is not induced, while that of OX18 is reduced. The level of ICAM-1 does not change. Furthermore, the average cell number of single colony is calculated from the recovered cell number, the percentage of rat hepatic cells and the colony efficiency. The estimated cell number reaches 3 to $4 \times 10^3$ (Table 2). This indicates that the single cell forming the colonies divided approximately 11-12 times on average under this culture condition.

TABLE 2

Calculation of the cell number in single hepatic colony.

| Inoculated cell number | Seeding density (cell/cm$^2$) | Culture length (day) | Recovered cell number | Percentage of rat cell (%) | Colony efficiency (%) | Average of cell number in single colony |
|---|---|---|---|---|---|---|
| 500 | 18 | 18 | $1.5 \times 10^6$ | 58 | 41 | $4.2 \times 10^3$ |
| 4000 | 51 | 21 | $6.0 \times 10^6$ | 90 | 44 | $3.1 \times 10^3$ |
| 4000 | 51 | 20 | $4.0 \times 10^6$ | 69 | 21 | $3.3 \times 10^3$ |

Figures 4, 4B:
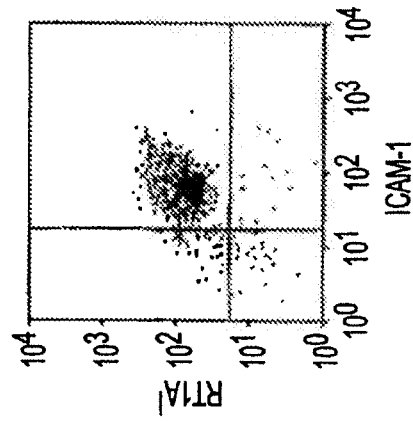
Figures 4, 4B, 5:
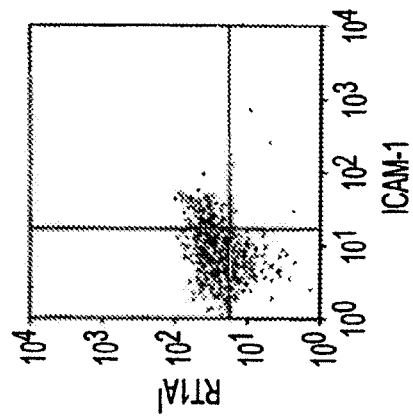
Figures 4, 4C:
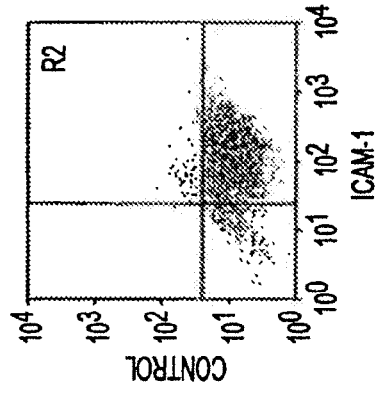
Figures 4, 4C, 5:
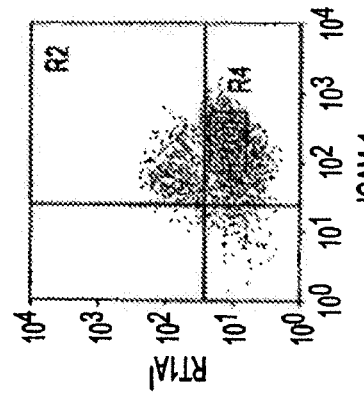
Figures 2, 4C:
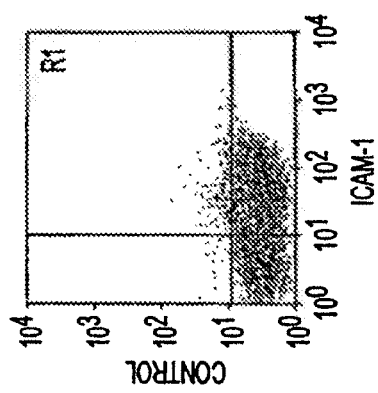
Figures 3, 4C:
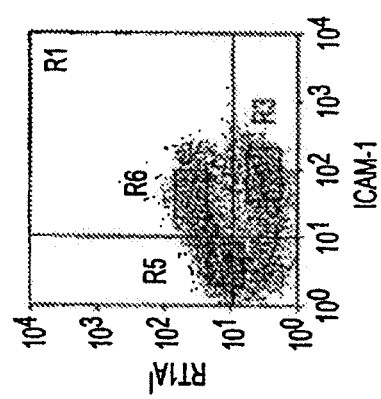
Figures 1, 4C:
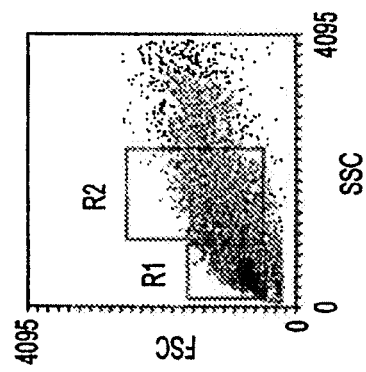
Figures 1, 4D:
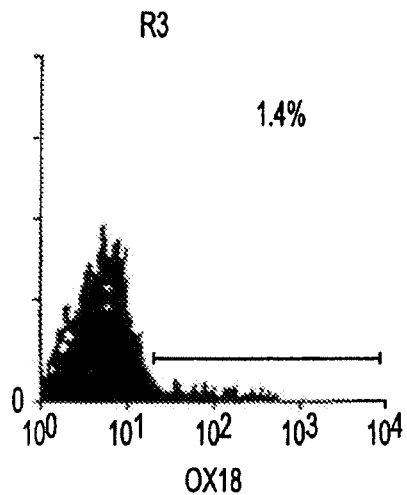
Figures 2, 4D:
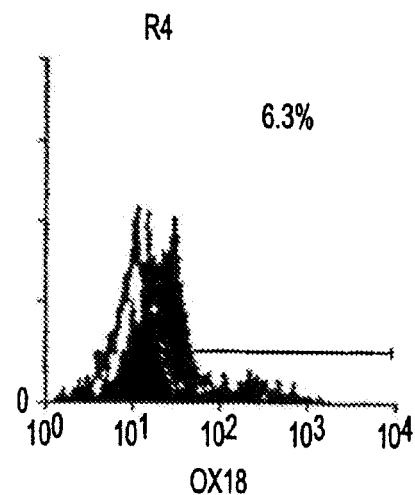
Figures 3, 4D:
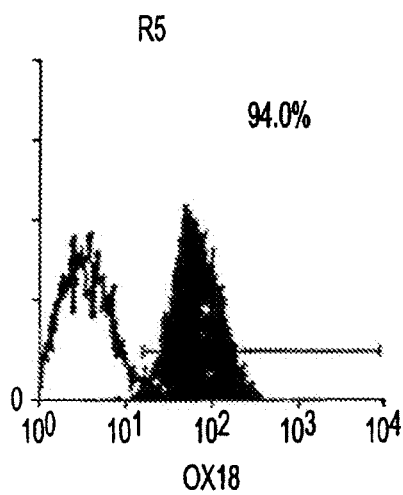
Figures 4, 4D:
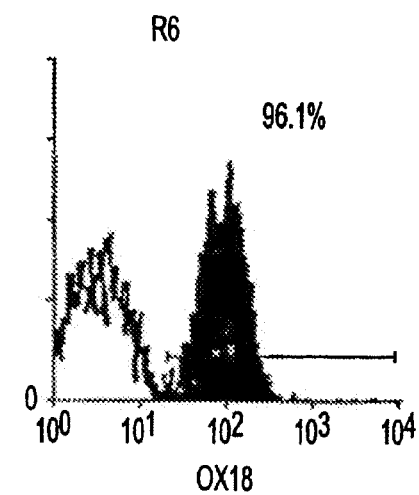

Sorted cells from R4 in FIG. 4C-5 were cultured on STO5hlx feeder cells in 60 mm or 100 mm dish. After the period indicated of the culture cell all cells were recovered and the total cell number counted. The percentage of rat cells is from flow cytometric analysis based on the expression of rat ICAM-1 and mouse CD98. Colony efficiency indicates the percentage of cells inoculated to culture that went on to form colonies. Data from triplicate-stained cultures (mean) was obtained from the experiments run parallel with. Average of cell number in single colony=(Recovered cell number×Percentage of rat cell/100)/Inoculated cell number×Colony efficiency/100)

6.6. Evidence for Bipotentiality in RT1A$^{1-}$ Hepatic Progenitors

At E13 of gestation in the rat, the hepatic cells are thought to have a bipotent precursor giving rise to the mature hepatocyte and bile duct epithelium. However, before the discoveries of the instant invention there has been no direct evidence whether the two fates originated from a single cell or not. To determine whether the RT1A$^{1-}$ OX18$^{dull}$ ICAM-1$^+$ fetal hepatic cells can differentiate to the biliary lineage in this culture system, the colonies are stained by anti-CK19 as a specific marker for biliary epithelial cells. CK19 is expressed in the bile duct epithelial precursors after day 15.5 in the fetal rat liver at which time the expression of albumin disappears in the cells. The sorted RT1A$^{1-}$ ICAM-1$^+$ cells are cultured in the presence or absence of EGF, and their fates are monitored by the expression of CK19 and albumin after 5 days of culture. After the first 5 days, the CK19$^+$ colonies are negligible in the cultures treated with EGF, whereas a few colonies containing CK19$^+$ cells occurred in those in the absence of EGF (FIG. 6a to 6b). Although the intensity of the CK19 expression is fairly weak, the CK19$^+$ cells show reduced albumin expression. At the 10th day of the culture, as shown in FIG. 6a to 6b, some colonies apparently express only CK19 or albumin and others have dual positive expression. The pattern of the CK19$^+$ and albumin$^+$ cells in a single colony is reciprocal. The number of dual positive colonies and CK19 single positive colonies still is higher in the absence of EGF (FIG. 6a). In the presence of EGF, many of the colonies consist only of albumin$^+$ cells at the 10th day (FIG. 6b). Eventually, the percentage of dual positive colonies reaches nearly 100% in the absence of EGF at day 15 (FIG. 6a). Altogether, EGF dramatically suppresses the appearance of CK19$^+$ colonies through the culture (FIG. 6b). These results suggest that the RT1A$^{1-}$, OX18$^{dull}$, and ICAM-1$^+$ cells from E13 fetal liver can differentiate towards the biliary lineage and their fate can be influenced by EGF in vitro (FIG. 7).

6.7. Isolation of Human and Non-Human Hepatic Precursors Using Antibodies to ICAM and Classical MHC Class I Epitopes.

The molecular structure and biological function of classical MHC class I antigens are highly conserved among vertebrates, and the same is the case for the ICAM antigens. However MHC antigens are not found in invertebrates. MHC antigens are the most comprehensively investigated molecules of vertebrate species. Although the information on ICAM antigens is limited, the biological functions of ICAM antigens are conserved in many mammals such as human mouse, and rat. So far, ICAM-1 complementary DNA has been cloned from human, chimpanzee, mouse, rat, dog, and bovine. The conclusion from the sequence data is that the molecular structure is highly conserved in all species. Therefore, by choosing antibodies specific for the ICAM-1 in a given species and antibodies for the designated class I MHC antigen according to the table, the cell populations enriched in hepatic progenitor cells can be isolated.

TABLE 3

Major Histocompatability Antigens - Nomenclature

| | Species | | |
|---|---|---|---|
| | Rats | Mice | Humans |
| MHC | RT1 | H-2 | HLA |
| Classical MHC class I | A | K, D, L | A, B, C |
| Nonclassical MHC class I | C/E, M | TL, Q, M | E, F, G, H, J, X |

OX18 recognizes a monomorphic epitope of rat MHC class I antigens. Therefore, the antibody recognizes nonclassical MHC class I as well as classical MHC class I. The exact number of nonclassical MHC class I loci are not defined in any species, because it varies between members of the same species. Therefore, in the future, a new locus might be discovered as a nonclassical MHC class I in subpopulations of these species.

One embodiment of the invention is a method of predicting the phenotype of hepatic progenitor cells. This feature is illustrated in the table of key cell surface markers in various species.

TABLE 4

Markers for Hepatic Progenitor Cells, based on the Instant Invention.

| | Species | | |
|---|---|---|---|
| | Rat | Mouse | Human |
| Classical MHC class I | RT1 A-Negative | H-2K negative and/or H-2D negative and/or H-2L negative | HLA-A negative and/or HLA-B negative and/or HLA-C negative |
| Nonclassical MHC class I | Dull positive for C/E and/or M | Dull positive for TL and/or Q and/or M | Dull positive for E, F, G, H, J, and/or X |
| ICAM-1 | Positive | Positive | Positive |

6.8. Characterization of Rat Bipotent Hepatic Progenitors and Comparison with Adult Hepatocytes

TABLE 5

Cell Surface and Internal Markers in Rat Cells.

| Markers | Bipotent Hepatic Cells | Adult Hepatocytes** |
|---|---|---|
| *Data From Freshly Isolated Cells* | | |
| ICAM-1 | + | + |
| CD90 (Thy-1) | − | − |
| CD44H | + | −* |
| Class I MHC (RT1Al) | − | + |
| OX 18 | Dull | + |
| *Data from Cultured Cells* | | |
| Alpha-fetoprotein | + | + in several of the cells in most colonies |
| Albumin | +EGF: many cells positive −EGF: fewer cells positive | + |
| CK19 | +EGF: few cells positive −EGF: many are positive | −*** |

EGF = epidermal growth factor that when added to the culture conditions appears to drive the cells towards the hepatocytic lineage and blocks development of the biliary lineage. In the absence of EGF, there is spontaneous differentiation towards both biliary and hepatocytic lineages.
*Others have shown that adult hepatocytes and adult biliary epithelia are negative for CD44H (Cruishank S M et al, J Clin Pathol 1999 52: 730-734) and CD 90 (Gordon G et al American Journal of Pathology 157: 771-786).
**Adult hepatocytes are those that can proliferate by hyperplastic growth in culture under the conditions specified above.
***CK 19 is not expressed on adult hepatocytes in vivo. However, in any culture of adult liver cells, one can observe one or two cells that express some CK19 but without apparent inducibility by culture conditions and without distinctions morphological between the positive and negative cells. This is in contrast to the observations in fetal liver in vivo and in the cultures of hepatic bipotent cells and of other fetal liver cells.

6.9. Antigenic Phenotyping of Human Fetal Liver Cells

Human fetal liver cells are stained with antibody to CD14. Several populations are identified by two-color cell sorting of HLA (ABC) vs. CD14. These populations include a group designated R2 characterized by intermediate HLA staining and without CD14 staining and another group designated R3 characterized by high CD14 staining and high HLA staining. When stained for alpha-feto protein, the R3 cells are positive for alpha-fetoprotein and the R2 contains two subpopulations, only one of which stains for AFP.

6.10. Further Isolation of Human Hepatic Precursors Using Antibodies to Expression Markers Including Nonclassical MHC Class I, Alpha-Fetoprotein, Albumin, and CK19.

In order to select monomorphic epitopes the cell suspension is incubated with fluorescein-conjugated antibody to the HLA class I monomorphic epitopes. The one skilled in the art will recognize that any of many other fluoro chromes can be used in place of fluorescein, including, but not limited to rhodamine and Texas Red. As an alternative indirect-immuno fluorescence is used to label the cells. That is, the fluorescent label is conjugated to an antibody directed to the immunoglobulin of the species in which the primary antibody is elicited. The cell sample is sorted by high throughput fluorescence-activated cell sorted using any of a variety of commercially available or customized cell sorter instruments. Hepatic progenitor cells that have intermediate or dull fluorescence with the labeled anti-monomorphic epitopes are selected.

Compositions enriched in rat hepatic progenitors can also be advantageously prepared by sorting liver cell suspensions using antibodies to CD44H. Liver cells that show a high level of sidescatter also express CD44H and express alpha fetoprotein. In particular, cells that express alpha-fetoprotein also express higher levels of CD44H. In contrast, liver cells that have a low level of sidescatter do not express CD44 at higher levels.

Liver cells that show a high level of sidescatter do not show a CD90-dependent distinction in alpha-fetoprotein expression. However, cells that show a low level of sidescatter show a CD90-dependent distinction in alpha-fetoprotein expression. In particular, the cells that express alpha-fetoprotein also express higher levels of CD90.

As an alternative, antibodies specific for polymorphic epitopes, including but not limited to, HLA-A2, HLA-B27, and HLA-Bw22, are used to identify and isolate hepatic progenitors.

Furthermore, antibodies specific for nonclassical HLA class I antigens, including HLA-G, HLA-E, and HLA-F, are used to identify and isolate hepatic progenitor cell that express the antigen.

It is evident that these methods are readily adaptable to non-mammalian hepatic progenitor cells.

6.11. Further Isolation of Human Hepatic Precursors Using High-Throughput Affinity Isolation Methods with Antibodies to expression markers including alpha-feto-protein, Albumin, Nonclassical MHC Class I and CK19

An isolation protocol is presented in diagrammatic form as follows:

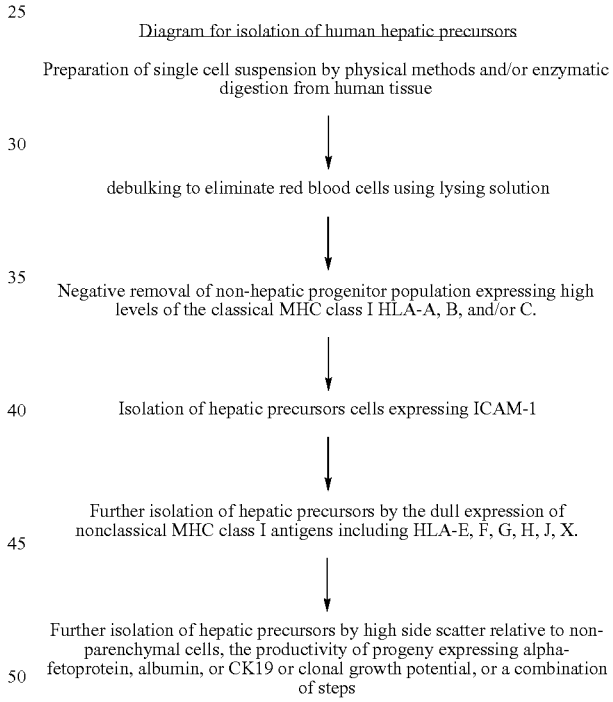

Other methods of debulking and eliminating the red blood cells component can be advantageously used and these methods can reduce some of the stromal cell population as well. These methods include fractionation on Percoll gradients and specific depletion using antibody to glycophorin A, CD45, or both. Furthermore, these methods include sedimentation velocity, separation in density gradients other than Percoll, e.g., Ficoll, zonal centrifugation and cell elutriation. By these methods red blood cells, polyploid hepatocytes, hemopoietic cells, and stromal cells are removed.

Isolation of cell populations that are positive for ICAM-1 and negative for classical MHC class I antigen are further characterized with other markers including nonclassical MHC class I to identify hepatic progenitors. In addition, the progeny of these progenitor cells labeled with antibodies to the cytoplasmic proteins, such as alpha-fetoprotein and/or albumin, markers that are long-known to be characteristic of hepatic progenitors. Alpha-fetoprotein and albumin are representative of the well known markers for hepatic progenitors that cannot be used to select for viable cells, since labeling the cells for those proteins requires permeabilization of the cells, a process that destroys their viability. However, cell samples from a population can be tested for alpha-fetoprotein, albumin, and cytokeratin. Thereby, the characteristics of the whole population are deduced. However, the high correlation between the cell surface markers (e.g., ICAM-1 positive, OX-18 dull positive, classical MHC class I negative) and clonal growth capability with the cytoplasmic markers alpha-fetoprotein, albumin, or CK19 demonstrates that viable cells can be isolated using selection for the surface markers alone.

6.12. Further Isolation of Human Hepatic Precursors Using Sidescatter.

Side scatter cannot be used, by itself, to identify a cell type such as the hepatic precursors. However, it is very useful as an adjunct to selection by other means such as fluorescence activated cell sorting for markers. For a population identified by a given marker, such as classical MHC class I, one must focus on a subpopulation defined by their side scatter characteristics (See FIG. 4c).

It is important to realize that mature hepatic cells are highly granular (show very high side scatter); the hepatic progenitors are intermediate in granularity; and the non-parenchymal cell populations have even less granularity than the hepatic precursors. In cells from fetal tissue, consisting almost entirely of non-parenchymal cells and hepatic progenitors, the hepatic progenitors have the highest granularity. Hepatic progenitors are selected as the cell population that is intermediate in granularity by flow cytometry.

Compositions enriched in human hepatic progenitors can also be advantageously prepared by sorting liver cell suspensions using antibodies to CD14 in combination with antibodies to HLA, the human version of MHC. All the methods of immunoselection are equally applicable. As a particular example, flow cytometry is used to isolate cells: cells designated R2 which express relatively intermediate levels of HLA and do not express CD14, and cells designated R3 which express relatively high levels of HLA and relatively high levels of CD14. The R2 cells are further characterized to have two subpopulations by expression of alpha-fetoprotein. The R3 cells are further characterized to consist only of cells that express alpha fetoprotein.

6.13. Removal of Non-Hepatic Progenitor Cells by Negative Selection with Antibodies to Glycophorin A or CD45.

The hepatic progenitors are distinguished from red blood cells by use of monoclonal antibodies (Glycophorin A for human) and a polyclonal antiserum to red blood cell antigen if monoclonal antibodies are not available. Also, cells that express common leukocyte antigen (CD45) also express classical MHC class I antigen. Therefore, by default, CD45 is not an antigen that can be used to identify the rodent hepatic progenitor cells but is used as an alternative or supplement to the negative selection by classical MHC class I.

6.14. Identification of Hepatic Cancers and Response to Treatment

The markers we have used to identify hepatic progenitors including nonclassical HLA class I antigens, ICAM-1 and alpha-fetoprotein can be used to characterize liver cancers to better define successful treatments of those cancers. Cancers, in general, are transformants of stem cells and early progenitor cell populations. However, these transformants often retain expression of the antigenic markers shared with their normal counterparts. Liver cancers, distinguished by these antigenic markers, can identify cancers responding in distinct ways to oncological therapeutic modalities (e.g., chemotherapeutic drugs, radiation, and adjuvant therapies).

6.15. Identification and Selection of Embryonic Stem Cells

The markers described here and the methodologies for selection can be also used to characterize the differentiation of embryonic stem (ES) cells to certain fates. ES cells are becoming popular as possible all-purpose stem cells for use in reconstitution of any tissue. However, past studies of injection of ES cells into tissues resulted in tumors, some of which were malignant. The only way the ES cells are to be used clinically is to differentiate them to determined stem cells and then inject the determined stem cells. Thus embryonic stem cells are maintained in cell culture under culture conditions that permit proliferation to form progeny. The ES progeny are subjected to flow cytometry after incubation with antibodies to classic MHC class I and ICAM-1 antigens. ES progeny meeting the criteria for hepatic progenitors are expanded in cell culture. The markers we have identified can be used to define an hepatic fate for a determined stem cell.

6.16. Use in Conjunction with Gene Therapy

The markers of liver progenitor cells identified here are used to identify cell populations for gene therapies. To date, gene therapies have often not worked or not worked well with targeting to mature cell populations. The major successes in gene therapies to date have been ex vivo gene therapies in hemopoietic progenitor cell populations. Therefore, ex vivo gene therapies for liver are used with hepatic-determined stem and progenitor cells isolated by our protocols. Also, the gene therapies involving "targeted injectable vectors" are improved by focusing on those that target hepatic progenitors. In these ways inborn errors of metabolism can be improved, including hemophilia, respiratory chain complex I deficiency, phenylketonuria, galactosemia, hepato-renal tyrosinemia, hereditary fructose intolerance, Wilson's disease, haemochromatosis, endoplasmic reticulum storage disease, hyperoxaluria type 1, 3 beta-hydroxy-delta 5-C27-steroid dehydrogenase deficiency, glycogen storage diseases (including deficiency of glucose-6-phosphatase, glucose-6-phosphate translocase, debranching enzyme, liver phosphorylase and phosphorylase-b-kinase), fatty acid oxidation or transfer defects (including organic acidurias, defects of acyl-CoA dehydrogenases), porphyria, and bilirubin uridine diphosphate glucuronyltransferase.

Hepatic progenitors can be used for gene therapy as follows:

Phenylketonuria (PKU) is an autosomal recessive disorder caused by a deficiency of phenylalanine hydroxylase (PAH) in the liver. PAH catalyzes the conversion of phenylalanine to tyrosine using tetrahydrobiopterin as a cofactor. Patients with PKU show profound mental retardation and hypopigmentation of skin, hair, and eyes due to increased amount of phenylalanine in body fluids. Although the rigid dietary restriction significantly reduces serum phenylalanine levels, reduced compliance, even in adolescence or early adulthood, often leads to a decline in mental or behavioral performance. Gene therapy technique is one alternative to dietary therapy for PKU. The development of a mutant mouse Pah$^{enu2}$ for PKU facilitated effects to attempt this approach. So far, three different vector systems, recombinant adenoviruses, retroviruses, and DNA/protein complexes have been developed. The effect of adenovirus-mediated gene transfer lasted for only short period after the injection because of the host immune response against the recombinant virus. Although recombinant retroviruses and DNA/protein complexes can effectively transduce PAH-deficient hepatocytes in vitro, the clinical utility of the ex-vivo approach is limited primarily because of the low number of cells that can be successfully reimplanted into liver. Use of hepatic progenitors with high growth potentiality can eliminate the problem mentioned above.

Diagram for Ex vivo Gene Therapy to Use Autologous Hepatic Progenitors

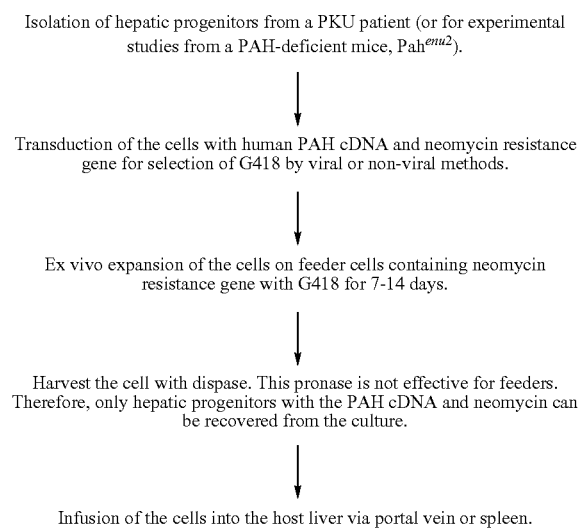

6.17. Use of Bipotent Hepatic Progentiors in Cell Therapy

A rat model of liver failure is used to evaluate heterogenous cell transplantation therapy. Liver failure is modeled by surgical removal of about 70% of the liver and ligation of the common bile duct in an experimental group of ten male rats (125 to 160 g body weight). A sham control group of ten age- and sex-matched rats is subjected to s similar anesthesia, mid-line laparotomy, and manipulation of the liver, but without ligation of the bile ducts and without hepatectomy.

An enriched population of hepatic precursors is prepared as described above. In brief, the livers of 12 embryonic (embryonic day 14) rat pups are aseptically removed, diced, rinsed in 1 mM EDTA in Hank's BSS without calcium or magnesium, pH 7.0, then incubated for up to 20 minutes in Hank's BSS containing 0.5 mg/ml collagenase to produce a near single cell suspension.

Bipotent hepatic progenitors are prepared by any of the above methods.

On day three after the hepatectomy or sham operation, the rats, both experimental and sham control, are subjected to a 5 mm abdominal incision to expose the spleen. One half of each of the experimental and sham control group animals, randomly chosen, are injected with 01.1 ml each of the bipotent hepatic progenitors composition, directly into the spleen. All incisions are closed with surgical staples. The number of cells administered to different groups of animals can be about $10^3$ up to about $10^{10}$, in particular, $10^3$, $10^4$, $10^5$, $10^6$, $10^7$, $10^8$, $10^9$ and $10^{10}$. The immunosuppressant cyclosporine A, 1 mg/kg body weight, is administered daily intraperitoneally.

Blood levels of bilirubin, gamma glutamyl transferase and alanine aminotransferase activities are monitored two days before the hepatectomy or sham hepatectomy operation and on post-operation days 3, 7, 14, and 28. Body weight, water consumption, and a visual inspection of lethargy are recorded on the same days. At 28 days post hepatectomy all surviving animals are killed for histological evaluation of spleen and liver.

The above examples have been depicted solely for the purpose of exemplification and are not intended to restrict the scope or embodiments of the invention. Other embodiments not specifically described should be apparent to those of ordinary skill in the art. Such other embodiments are considered to fall, nevertheless, within the scope and spirit of the present invention. Thus, the invention is properly limited solely by the claims that follow.

The invention claimed is:

1. An isolated single-cell bipotent hepatic progenitor which
   (a) expresses at least one intercellular adhesion molecule (ICAM) antigen;
   (b) does not express major histocompatibility complex (MHC) class Ia antigen;
   (c) expresses alpha-fetoprotein, albumin and CK19; and
   (d) exhibits weak expression of a MHC class Ib antigen, as compared to non-parenchymal cells as measured in a flow cytometer, wherein the bipotent hepatic progenitor has a capacity to differentiate into a hepatocyte or a biliary cell when exposed to differentiation-inducing growth conditions.

2. A composition consisting essentially of isolated single-cell bipotent hepatic progenitors which
   (a) expresses at least one intercellular adhesion molecule (ICAM) antigen;
   (b) does not express major histocompatibility complex (MHC) class Ia antigen;
   (c) expresses alpha-fetoprotein, albumin and CK19; and
   (d) exhibits weak expression of a MHC class Ib antigen, as compared to non-parenchymal cells as measured in a flow cytometer, wherein the bipotent hepatic progenitor has a capacity to differentiate into a hepatocyte or a biliary cell when exposed to differentiation-inducing growth conditions.

3. A composition consisting essentially of isolated single-cells enriched bipotent hepatic progenitors which
   (a) expresses at least one intercellular adhesion molecule (ICAM) antigen;
   (b) does not express major histocompatibility complex (MHC) class Ia antigen;
   (c) expresses alpha-fetoprotein, albumin and CK19; and
   (d) exhibits weak expression of a MHC class Ib antigen, as compared to non-parenchymal cells as measured in a flow cytometer, wherein the bipotent hepatic progenitor has a capacity to differentiate into a hepatocyte or a biliary cell when exposed to differentiation-inducing growth conditions.

4. The composition of claim 3, wherein the hepatic progenitor cell exhibits weak expression of MHC class Ib antigen in comparison to the expression of ICAM antigen as indicated by immunostaining.

5. The composition of claim 3 in which the ICAM antigen is ICAM-1.

6. The composition of claim 3 in which the hepatic progenitor have a sidescatter value determined by flow cytometry which is numerically less than the sidescatter value of mature parenchymal cell of the same species.

7. The composition of claim 3 in which the hepatic progenitor have a sidescatter in flow cytometry which is between the sidescatter of nonparenchymal cells of the same species and the sidescatter of mature parenchymal cell of the same species.

8. The composition of claim 3 in which the hepatic progenitor are capable of dividing and giving rise to progeny.

9. The composition of claim 8 in which the hepatic progenitor exhibit a capacity for clonal growth.

10. The composition of claim 9 further comprising an extracellular matrix.

11. The composition of claim 3 in which the hepatic progenitors are derived from endoderm or bone marrow.

12. the composition of claim 11 in which the endoderm is selected from liver, pancreas, lung, gut, thyroid, gonad, or combinations therof.

13. The hepatic progenitor of claim 1 in which the ICAM antigen is ICAM-1.

14. The hepatic progenitor of claim 1, wherein the hepatic progenitor cell exhibits weak expression of MHC class Ib antigen in comparison to the expression of ICAM antigen as indicated by immunostaining.

15. A cell culture comprising a population of single-cell bipotent hepatic progenitors that
(a) expresses at least one intercellular adhesion molecule (ICAM) antigen;
(b) does not express major histocompatibility complex (MHC) class Ia antigen;
(c) expresses alpha-fetoprotein, albumin and CK19; and
(d) exhibits weak expression of a MHC class Ib antigen, as compared to non-parenchymal cells as measured in a flow cytometer, wherein the bipotent hepatic progenitor has a capacity to differentiate into a hepatocyte or a biliary cell when exposed to differentiation-inducing growth conditions.

16. The cell of claim 15 further comprising extracellular matrix.

17. The cell culture of claim 16 in which the extracellular matrix comprises collagen, fibronectin, laminin, or combinations thereof.

18. The cell culture of claim 16 further comprising feeder cells.

19. The cell culture of claim 18 in which the feeder cells are fibroblast cells.

20. The cell culture of claim 18 in which the feeder cells are embryonic or fetal cells.

21. The cell culture of claim 16 further comprising a serum-free culture medium.

* * * * *